United States Patent
Verdine et al.

(10) Patent No.: US 10,989,710 B2
(45) Date of Patent: *Apr. 27, 2021

(54) IDENTIFYING NEW THERAPEUTIC AGENTS

(71) Applicant: Revolution Medicines, Inc., Redwood City, CA (US)

(72) Inventors: Gregory L. Verdine, Boston, MA (US); David W. White, Norwell, MA (US); David M. Armistead, Sudbury, MA (US); Deborah J. Palestrant, Newton, MA (US); Brian Y. Chow, Cambridge, MA (US); Chris K. Varma, Cambridge, MA (US); Mathew Edward Sowa, Watertown, MA (US)

(73) Assignee: Revolution Medicines, Inc., Redwood City, CA (US)

( * ) Notice: Subject to any disclaimer, the term of this patent is extended or adjusted under 35 U.S.C. 154(b) by 77 days.

This patent is subject to a terminal disclaimer.

(21) Appl. No.: 16/227,828

(22) Filed: Dec. 20, 2018

(65) Prior Publication Data

US 2019/0271691 A1 Sep. 5, 2019

Related U.S. Application Data

(63) Continuation of application No. 15/226,480, filed on Aug. 2, 2016, now Pat. No. 10,203,323, which is a continuation of application No. 13/337,875, filed on Dec. 27, 2011, now Pat. No. 9,428,845.

(60) Provisional application No. 61/427,626, filed on Dec. 28, 2010.

(51) Int. Cl.
| | |
|---|---|
| *G01N 33/50* | (2006.01) |
| *G01N 33/53* | (2006.01) |
| *C40B 30/04* | (2006.01) |
| *G01N 33/68* | (2006.01) |

(52) U.S. Cl.
CPC ......... *G01N 33/5308* (2013.01); *C40B 30/04* (2013.01); *G01N 33/68* (2013.01); *G01N 33/6848* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 6,183,965 B1 | 2/2001 | Verdine et al. | |
| 6,372,712 B1 | 4/2002 | Briesewitz et al. | |
| 6,713,607 B2 | 3/2004 | Caggiano et al. | |
| 7,220,552 B1 | 5/2007 | Crabtree et al. | |
| 8,664,186 B2 | 3/2014 | Aigle et al. | |
| 9,250,237 B2 | 2/2016 | Liu et al. | |
| 9,428,845 B1 | 8/2016 | Verdine et al. | |
| 10,203,323 B2 * | 2/2019 | Verdine | G01N 33/5308 |
| 2002/0110874 A1 | 8/2002 | Khosla et al. | |
| 2002/0147133 A1 | 10/2002 | Briesewitz et al. | |
| 2003/0153053 A1 | 8/2003 | Reid | |
| 2003/0175901 A1 | 9/2003 | Reeves et al. | |
| 2004/0087496 A1 | 5/2004 | Kim et al. | |
| 2005/0233431 A1 | 10/2005 | Ashley et al. | |
| 2007/0203168 A1 | 8/2007 | Zhao | |
| 2011/0117606 A1 | 5/2011 | Jorgensen et al. | |
| 2012/0208720 A1 | 8/2012 | Kashiwagi et al. | |
| 2012/0270800 A1 | 10/2012 | Verdine et al. | |
| 2013/0072439 A1 | 3/2013 | Nash et al. | |
| 2014/0073581 A1 | 3/2014 | Liu et al. | |
| 2015/0250896 A1 | 9/2015 | Zhao | |
| 2015/0307855 A1 | 10/2015 | Yuzawa et al. | |
| 2016/0341719 A1 | 11/2016 | Verdine et al. | |

FOREIGN PATENT DOCUMENTS

| | | |
|---|---|---|
| EP | 0393934 A1 | 10/1990 |
| EP | 0562853 A1 | 9/1993 |
| EP | 1079859 B1 | 7/2010 |
| KR | 10-2009-0041971 A | 4/2009 |
| WO | WO-86/02080 A1 | 4/1986 |
| WO | WO-95/32294 A1 | 11/1995 |
| WO | WO-96/020216 A1 | 7/1996 |
| WO | WO-98/07743 A1 | 2/1998 |
| WO | WO-98/12217 A1 | 3/1998 |
| WO | WO-99/61055 A1 | 12/1999 |
| WO | WO-01/36460 A2 | 5/2001 |
| WO | WO-01/36612 A1 | 5/2001 |
| WO | WO-01/90070 A2 | 11/2001 |
| WO | WO-03/033010 A1 | 4/2003 |
| WO | WO-2008/069824 A2 | 6/2008 |
| WO | WO-2010/031185 A1 | 3/2010 |
| WO | WO-2010/034243 A1 | 4/2010 |
| WO | WO-2010/088573 A1 | 8/2010 |
| WO | WO-2012/075048 A2 | 6/2012 |
| WO | WO-2012/174489 A2 | 12/2012 |
| WO | WO-2014/009774 A1 | 1/2014 |
| WO | WO-2014/187959 A2 | 11/2014 |
| WO | WO-2015/132784 A1 | 9/2015 |
| WO | WO-2018/081592 A2 | 5/2018 |

OTHER PUBLICATIONS

"Streptomyces iranensis regulatory protein LuxR," EBI Database Accession No. CDR13506 (2014) (2 pages).
"Streptomyces rapamycinicus NRRL 5491 hypothetical protein," EBI Database Accession No. AGP59507 (2014) (2 pages).
Baranasic et al., "Draft Genome Sequence of Streptomyces rapamycinicus Strain NRRL 5491, the Producer of the Immunosuppressant Rapamycin," Genome Announc. 1(4):e000581-13 (2013) (2 pages).
He et al., "The LuxR family members GdmRI and GdmRII are positive regulators of geldanamycin biosynthesis in Streptomyces hygroscopicus 17997," Arch Microbiol. 189(5):501-10 (2008).
Horn et al., "Draft Genome Sequence of Streptomyces iranensis," Genome Announc. 2(4):e00616-14 (2014) (2 Pages).
Laureti et al., Supporting Material for "Identification of a bioactive 51-membered macrolide complex by activation of a silent polyketide synthase in Streptomyces ambofaciens," Proc Natl Acad Sci U.S.A. 108(15):6258-63 (2011), accessed via <https://www.pnas.org/content/suppl/2011/03/24/1019077108.DCSupplemental> (41 pages).

(Continued)

*Primary Examiner* — Ronald T Niebauer
(74) *Attorney, Agent, or Firm* — Clark & Elbing LLP

(57) ABSTRACT

Disclosed herein are methods for identifying novel drug candidates.

6 Claims, 2 Drawing Sheets

(56) References Cited

OTHER PUBLICATIONS

Mo et al., "Interspecies Complementation of the LuxR Family Pathway-Specific Regulator Involved in Macrolide Biosynthesis," J Microbiol Biotechnol. 26(1):66-71 (2016).
U.S. Appl. No. 61/418,038, Johns Hopkins University.
"SMART™ Drugs: Engineering Nature's Solution to the Undruggable Target Challenge," WarpDrive Bio, 2016, available <http://www.warpdrivebio.com/docs/Warp%20Drive%20Bio_SMART%20Drugs%20Platform_2016.pdf> (31 pages).
"Substructure Search Report on Specifically Substituted Macrocycles—Substances Only", prepared by Science IP, dated Dec. 17, 2014 (6177 pages).
Allain et al., "Cyclophilin B mediates cyclosporin A incorporation in human blood T-lymphocytes through the specific binding of complexed drug to the cell surface," Biochem J. 317 (Pt 2):565-70 (1996).
Andrei et al., "Stabilization of protein-protein interactions in drug discovery," Expert Opin Drug Discov. 12(9):925-40 (2017) (17 pages).
Antunes et al., "A mutational analysis defines Vibrio fischeri LuxR binding sites," J Bacteriol. 190(13):4392-7 (2008).
Archibald et al., "Discovery and Evaluation of Potent, Cysteine-based alpha4beta1 Integrin Antagonists," Bioorg Med Chem Lett. 10(9):993-995 (2000).
Banaszynski et al., "Characterization of the FKBP.rapamycin.FRB ternary complex," J Am Chem Soc. 127(13):4715-21 (2005).
Bayle et al., "Rapamycin analogs with differential binding specificity permit orthogonal control of protein activity," Chem Biol. 13(1):99-107 (2006).
Bender et al., "Periodate Oxidation of alpha-Keto gamma-Lactams. Enol Oxidation and beta-Lactam Formation. Mechanism of Periodate Hydrozylation Reactions," J Org Chem. 43(17):3354-3362 (1978).
Benjamin et al., "Rapamycin passes the torch: a new generation of mTOR inhibitors," Nat Rev Drug Discov. 10(11):868-80 (2011).
Bhuyan et al., "Antioxidant activity of peptide-based angiotensin converting enzyme inhibitors," Org. Biomol. Chem. 10(11):2237-47 (2012).
Blodgett et al., "Unusual transformations in the biosynthesis of the antibiotic phosphinothricin tripeptide," Nat Chem Biol. 3(8):480-5 (2007).
Briesewitz et al., "Affinity modulation of small-molecule ligands by borrowing endogenous protein surfaces," Proc Natl Acad Sci U.S.A. 96(5):1953-8 (1999).
Bruce, "In vivo protein complex topologies: sights through a cross-linking lens," Proteomics. 12(10):1565-75 (2012).
Burgess et al., "Controlled translocation of palladium(II) within a 22 ring atom macrocyclic ligand," Dalton Trans. 43(45):17006-16 (2014).
Chaurasia et al., "Molecular insights into the stabilization of protein-protein interactions with small molecule: The FKBP12-rapamycin-FRB case study," Chem Phys Lett. 587:68-74 (2013).
Che et al., "Inducing protein-protein interactions with molecular glues," Bioorganic & Medicinal Chemistry Letters (2018).
Chevalier et al., "Straightforward synthesis of bioconjugatable azo dyes. Part 1: Black Hole Quencher-1 (BHQ-1) scaffold," Tetrahedron Lett. 55(50):6759-63 (2014).
Findlay et al., "The structure of demethoxyrapamycin," Can J Chem. 60:2046-7 (1982).
Guerra et al., "LAL regulators SCO0877 and SCO7173 as pleiotropic modulators of phosphate starvation response and actinorhodin biosynthesis in Streptomyces coelicolor," PLoS One. 7(2):e31475 (2012) (11 pages).
Horton et al., "Engineering hybrid genes without the use of restriction enzymes: gene splicing by overlap extension," Gene. 77(1):61-8 (1989).
Hosted et al., "Use of rpsL for dominance selection and gene replacement in *Streptomyces roseosporus*," J Bacteriol. 179(1):180-6 (1997).

Huang et al., "Conjugation to Albumin-Binding Molecule Tags as a Strategy to Improve Both Efficacy and Pharmacokinetic Properties of the Complement Inhibitor Compstatin," ChemMedChem. 9(10):2223-6 (2014).
Huang et al., "Enhanced rapamycin production in *Streptomyces hygroscopicus* by integrative expression of aveR, a LAL family transcriptional regulator," World J Microbiol Biotechnol. 27:2103-9 (2011).
Hubler et al., "Synthetic routes to NEtXaa4-cyclosporin A derivatives as potential anti-HIV I drugs," Tetrahedron Lett. 41:7193-6 (2000).
Ishizawa et al., "TRAP display: a high-speed selection method for the generation of functional polypeptides," J Am Chem. 135(14):5433-40 (2013).
Kawakami et al., "In vitro selection of multiple libraries created by genetic code reprogramming to discover macrocyclic peptides that antagonize VEGFR2 activity in living cells," ACS Chem Biol. 8(6):1205-14 (2013).
Kendrew et al., "Recombinant strains for the enhanced production of bioengineered rapalogs," Metab Eng. 15:167-73 (2013).
Kuhn et al., "Synthesis of Functional Ras Lipoproteins and Fluorescent Derivatives," J Am Chem Soc. 123(6):1023-35 (2001).
Kuramochi et al., "Identification of Small Molecule Binding Molecules by Affinity Purification Using a Specific Ligand Immobilized on PEGA Resin," Bioconjug. Chem. 19(12):2417-26 (2008).
Laureti et al., "Identification of a bioactive 51-membered macrolide complex by activation of a silent polyketide synthase in Streptomyces ambofaciens," Proc Natl Acad Sci USA. 108(15):6258-63 (2011).
Leskiw et al., "TTA codons in some genes prevent their expression in a class of developmental, antibiotic-negative, *Streptomyces* mutants," Proc Natl Acad Sci USA. 88(6):2461-5 (1991).
Li et al., "A simple and efficient route to the FKBP-binding domain from rapamycin," available in PMC Sep. 28, 2012, published in final edited form as: Tetrahedron Lett. 52(39):5070-2 (2011) (7 pages).
Luengo et al., "Structure-activity studies of rapamycin analogs: evidence that the C-7 methoxy group is part of the effector domain and positioned at the FKBP12-FRAP interface," Chem Biol. 2(7):471-81 (1995).
Meyer et al., "Selective palladation of a large (32 ring atom) macrocyclic ligand at a bis(N-heterocyclic carbene) coordination pocket through transmetallation of the corresponding mercury(II) derivative," Dalton Trans. 41(46):14059-67 (2012).
Ochi et al., "New strategies for drug discovery: activation of silent or weakly expressed microbial gene clusters," Appl Microbiol Biotechnol. 97(1):87-98 (2013).
Papageorgiou et al., "Improved binding affinity for cyclophilin A by a cyclosporin derivative singly modified at its effector domain," J Med Chem. 37(22):3674-6 (1994).
Pfeifer et al., "Biosynthesis of complex polyketides in a metabolically engineered strain of *E. coli*," Science 291(5509):1790-2 (2001).
Quesniaux et al., "Cyclophilin binds to the region of cyclosporine involved in its immunosuppressive activity," Eur J Immunol. 17(9):1359-65 (1987).
Quesniaux et al., "Study of the conformation of cyclosporine in aqueous medium by means of monoclonal antibodies," Int J Pept Protein Res. 31(2):173-85 (1988).
Ranganathan et al., "Knowledge-based design of bimodular and trimodular polyketide synthases based on domain and module swaps: a route to simple statin analogues," Chem Biol. 6(10):731-41 (1999).
Revill et al., "Genetically engineered analogs of ascomycin for nerve regeneration," J Pharmacol Exp Ther. 302(3):1278-85 (2002).
Ruan et al., "Binding of rapamycin analogs to calcium channels and FKBP52 contributes to their neuroprotective activities," Proc Natl Acad Sci U.S.A. 105(1):33-8 (2008).
Schwecke et al., "The biosynthetic gene cluster for the polyketide immunosuppressant rapamycin," Proc Natl Acad Sci USA. 92(17):7839-43 (1995).
Sieber et al., "Novel inhibitors of the calcineurin/NFATc hub—alternatives to CsA and FK506?," Cell Commun Signal. 7:25 (2009) (19 pages).

(56) References Cited

OTHER PUBLICATIONS

Smulik et al., "Synthesis of cyclosporin A-derived affinity reagents by olefin metathesis," Org Lett. 4(12):2051-4 (2002).

STN record of WO 2014/009774, available online Jan. 16, 2014 (4 pages).

STN record of WO 98/12217, available online Mar. 26, 1998 (6 pages).

Sweeney et al., "From chemical tools to clinical medicines: non-immunosuppressive cyclophilin inhibitors derived from the cyclosporin and sanglifehrin scaffolds," J Med Chem. 57(17):7145-59 (2014) (63 pages).

Takakusagi et al., "Efficient one-cycle affinity selection of binding proteins or peptides specific for a small-molecule using a T7 phage display pool," Bioorg. Med. Chem. 16(22):9837-46 (2008).

UniProtKB Accession No. A0A061A6I8, Sep. 3, 2014, available <http://www.uniprot.org/uniprot/A0A061A6I8>, (12 pages).

UniProtKB Accession No. Q54296, Nov. 1, 1996, available <http://www.uniprot.org/uniprot/Q54296>, (12 pages).

UniProtKB Accession No. Q54297, Nov. 1, 1996, available <https://www.uniprot.org/uniprot/Q54297.txt>, (3 pages).

Vignot et al., "mTOR-targeted therapy of cancer with rapamycin derivatives," Ann Oncol. 16(4):525-37 (2005).

Wagner et al., "New naturally occurring amino acids," Angew Chem Int Ed Engl. 22:816-28 (1983).

Wang et al., "Thermodynamic analysis of cyclosporin a binding to cyclophilin a in a lung tumor tissue lysate," Anal Chem. 76(15):4343-8 (2004).

Wilson et al., "Comparative X-ray structures of the major binding protein for the immunosuppressant FK506 (tacrolimus) in unliganded form and in complex with FK506 and rapamycin," Acta Cryst. D51:511-21 (1995).

Wright et al., "Multivalent binding in the design of bioactive compounds," Curr Org Chem. 5(11):1107-31 (2001).

Wu et al., "Creating diverse target-binding surfaces on FKBP12: synthesis and evaluation of a rapamycin analogue library," available in PMC Sep. 12, 2012, published in final edited form as: ACS Comb Sci. 13(5):486-95 (2011) (22 pages).

Wu et al., "Inhibition of ras-effector interactions by cyclic peptides," Med Chem Commun. 4(2):378-82 (2013).

Wu et al., "Synthesis of Ketone Analogues of Prolyl and Pipecolyl Ester FKBP12 Ligands," J Med Chem. 45(16):3558-3568 (2002).

\* cited by examiner

IDENTIFYING NEW THERAPEUTIC AGENTS

CROSS REFERENCE TO RELATED APPLICATIONS

The present application claims priority to U.S. provisional application Ser. No. 61/427,626, filed Dec. 28, 2010, the entire contents of which are hereby incorporated herein by reference.

BACKGROUND OF THE INVENTION

The vast majority of small molecule drugs act by binding a functionally important site on a target protein, thereby modulating the activity of that protein. For example, the cholesterol-lowering drugs statins bind the enzyme active site of HMG-CoA reductase, thus preventing the enzyme from engaging with its substrates The fact that many such drug/target interacting pairs are known may have misled some into believing that a small molecule modulator could be discovered for most, if not all, proteins provided a reasonable amount of time, effort, and resources. This is far from the case. Current estimates hold that only about 10% of all human proteins are targetable by small molecules. The other 90% are currently considered refractory or intractable toward small molecule drug discovery. Such targets are commonly referred to as "undruggable." Wolfson, Chemistry & Biology 16, 2009, 910-12. These undruggable targets include a vast and largely untapped reservoir of medically important human proteins. Thus, there exists a great deal of interest in discovering new molecular modalities capable of modulating the function of such undruggable targets.

Small molecules are limited in their targeting ability because their interactions with the target are driven by adhesive forces, the strength of which is roughly proportional to contact surface area. Because of their small size, the only way for a small molecule to build up enough intermolecular contact surface area to effectively interact with a target protein is to be literally engulfed by that protein. Indeed, a large body of both experimental and computational data supports the view that only those proteins having a hydrophobic "pocket" on their surface are capable of binding small molecules. In those cases, binding is enabled by engulfment. Not a single example exists of a small molecule binding with high-affinity to a protein outside of a hydrophobic pocket.

Nature has evolved a completely unique strategy that allows a small molecule to interact with target proteins at sites other than hydrophobic pockets. This strategy, typified by the naturally occurring immunosuppressive drugs cyclosporine A, rapamycin, and FK506, initially involves the formation of a high-affinity complex of the small molecule with a small presenting protein. The composite surface of the small molecule and the presenting protein then engages the target. Thus, for example, the binary complex formed between cyclosporin A and cyclophilin A targets calcineurin with high affinity and specificity, but neither cyclosporin A or cyclophilin A alone binds calcineurin with measurable affinity.

Many important therapeutic targets exert their function by completion with other proteins. The protein/protein interaction surfaces in many of these systems contain an inner core of hydrophobic side chains surrounded by a wide ring of polar residues. The hydrophobic residues contribute nearly all of the energetically favorable contacts, and hence this cluster has s been designated as a "hotspot" for engagement in protein-protein interactions. Importantly, in the aforementioned complexes of naturally occurring small molecules with small presenting proteins, the small molecule provides a cluster of hydrophobic functionality akin to a hotspot, and the protein provides the ring of mostly polar residues. In other words, presented small molecule systems mimic the surface architecture employed widely in natural protein/protein interaction systems.

Nature has demonstrated the ability to reprogram the target specificity of presented small molecules—portable hotspots—through evolutionary diversification. In the best characterized example, the complex formed between FK506 binding protein (FKBP) and FK506 targets calcineurin. However, FKBP can also form a complex with the related molecule rapamycin, and that complex interacts with a completely different target, TorCl. To date, no methodology has been developed to reprogram the binding and modulating ability of presenter protein/ligand interfaces so that they can interact with and modulate other target proteins that have previously been considered undruggable.

In addition, it is well established that some drug candidates fail because they modulate the activity of both the intended target and other non-intended proteins as well. The problem is particularly daunting when the drug binding site of the target protein is similar to binding sites in non-target proteins. The insulin like growth factor receptor (IGF-1R), whose ATP binding pocket is structurally similar to the binding pocket of the non-target insulin receptor (IR), is one such example. Small molecule development candidates that were designed to target IGF-1R typically have the unacceptable side effect of also modulating the insulin receptor. However, structural dissimilarities do exist between these two proteins in the regions surrounding the ATP binding pocket. Despite such knowledge, no methodology exists to date to take advantage of those differences and develop drugs that are specific to IGF-1R over IR.

SUMMARY OF THE INVENTION

The present invention provides, among other things, methods of identifying a compound which, when complexed to a presenter protein, modulates a biological activity of a target protein. In some embodiments, such a method comprises contacting at least one Test. Compound with a presenter protein and with a target protein, and assessing to what extent the Test Compound modulates (e.g., enhances or interferes with) formation of a complex comprising both the presenter protein and the target protein.

In general, a Test Compound has a structure that comprises both Presenter Interacting Sites and Target Interacting Sites. Together, the Presenter interacting Sites mediate binding between the Test Compound and the presenter protein by making contacts with corresponding interacting sites on the presenter protein; the Target interacting sites mediate binding between the Test Compound and the target protein by making contacts with corresponding interacting sites on the target protein. In some embodiments, the presenter and target proteins make one or more direct contacts with one another.

In some embodiments, provided methods comprise the steps of:
  a) Contacting a Test Compound with a presenter protein under conditions suitable for formation of a binary complex comprising the Test Compound and the presenter protein,
  b) Contacting a binary complex with a target protein, c) Assessing extent of formation and/or stability of a complex comprising both the presenter protein and the target protein when the Test Compound is present as compared to when it is absent, and determining whether presence of the Test Compound alters such extent of formation and/or stability.

In some embodiments, there is no detectable formation of a complex comprising both a presenter protein and a target protein in the absence of a Test Compound. In some embodiments, the amount and/or stability of such complex formation is increased in the presence of a Test Compound. In some embodiments, the amount and/or stability of such complex formation is decreased in the presence of a Test Compound.

In some embodiments, a target protein has greater affinity for a binary complex relative to the affinity of a target protein for a presenter protein in the absence of a binary complex. An increase in the affinity of a binary complex for a target protein indicates that a Test Compound can modulate the activity of a target protein. In some embodiments, a binary complex antagonizes the activity of a target protein. In some embodiments, a binary complex agonizes the activity of a target protein.

In some embodiments, provided such methods can be used to identify a compound which when complexed to a presenter protein modulates a biological activity of a target protein. In some embodiments, provided such methods can be used to identify a target protein whose biological activity is modulated by a Test Compound.

Another embodiment of the invention is a method of developing a drug candidate with modified selectivity towards a first target protein relative to a second target protein from a modulator compound that modulates the activity of both the first and second target protein. The method comprises the following steps:
a) providing a ligand compound and a presenter protein, wherein:
  i) the ligand compound comprises a Presenter Interacting Moiety that binds to the presenter protein to form a binary complex; and a Target Interacting Moiety which enhances the affinity of the binary complex for a first target protein relative to the affinity of the presenter protein for the first target protein in the absence of the binary complex; and
  ii) the binary complex does not substantially bind to a second target protein;
b) covalently associating a modulator compound with the Target Interacting Moiety of the ligand compound to form a modified ligand compound;
c) contacting the modified ligand compound with the presenter protein under conditions that allow the presenter protein to bind to the modified ligand compound to form a modified binary complex;
d) measuring the activity of the first target protein in the presence of the modified binary complex and measuring the activity of the first target protein in the presence of the modulator compound;
e) measuring the activity of the second target protein in the presence of the modified binary complex and measuring the activity of the second target protein in the presence of the modulator compound;
f) comparing the activity of the first and second target protein in the presence of the modified binary complex and comparing to the activity of the first and second target protein in the presence of the modulator compound to assess whether the modified binary complex has altered selectivity towards the first target protein relative to the second target protein compared with a modulator compound.

Yet another embodiment of the invention is a method of creating a modulator-based compound having modified selectivity towards a first target protein relative to a second target protein, from a modulator that modulates the activity of both a first and second target protein. The method comprises the following steps:
a) providing a ligand compound, wherein:
  i) a ligand compound comprises a Presenter Interacting Moiety that binds to a presenter protein to form a binary complex; and a Target interacting Moiety which enhances the affinity of the binary complex for a first target protein relative to the affinity of the presenter protein for the first target protein in the absence of the binary complex; and
  ii) the binary complex does not substantially bind to a second target protein; and
b) covalently associating the modulator compound with the Target Interacting Moiety of a ligand compound thereby creating a modulator-based compound.

DETAILED DESCRIPTION OF THE PREFERRED EMBODIMENTS

Definitions

Figure 1:
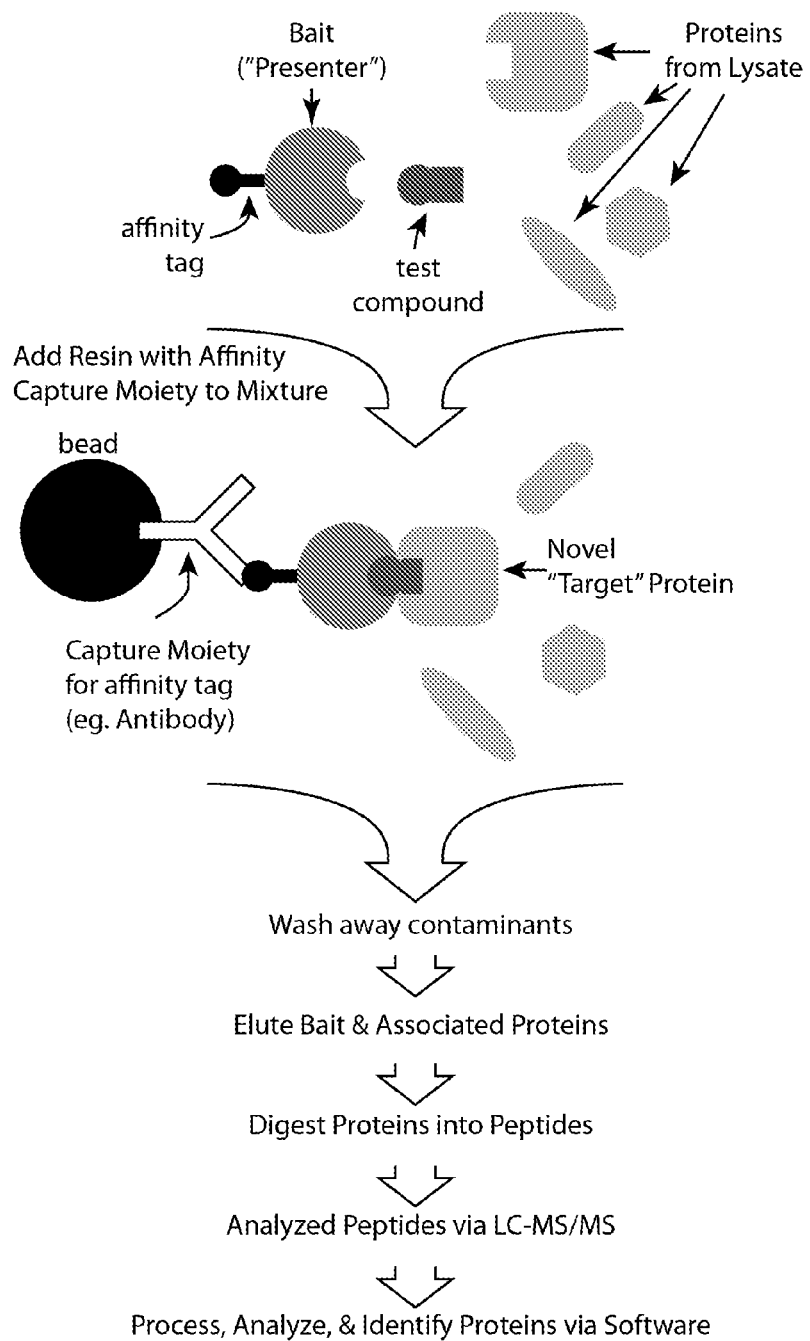
FIG. 1 is a schematic showing affinity purification of protein complexes followed by mass spectrometric analysis allowing for target identification.
Figure 2:
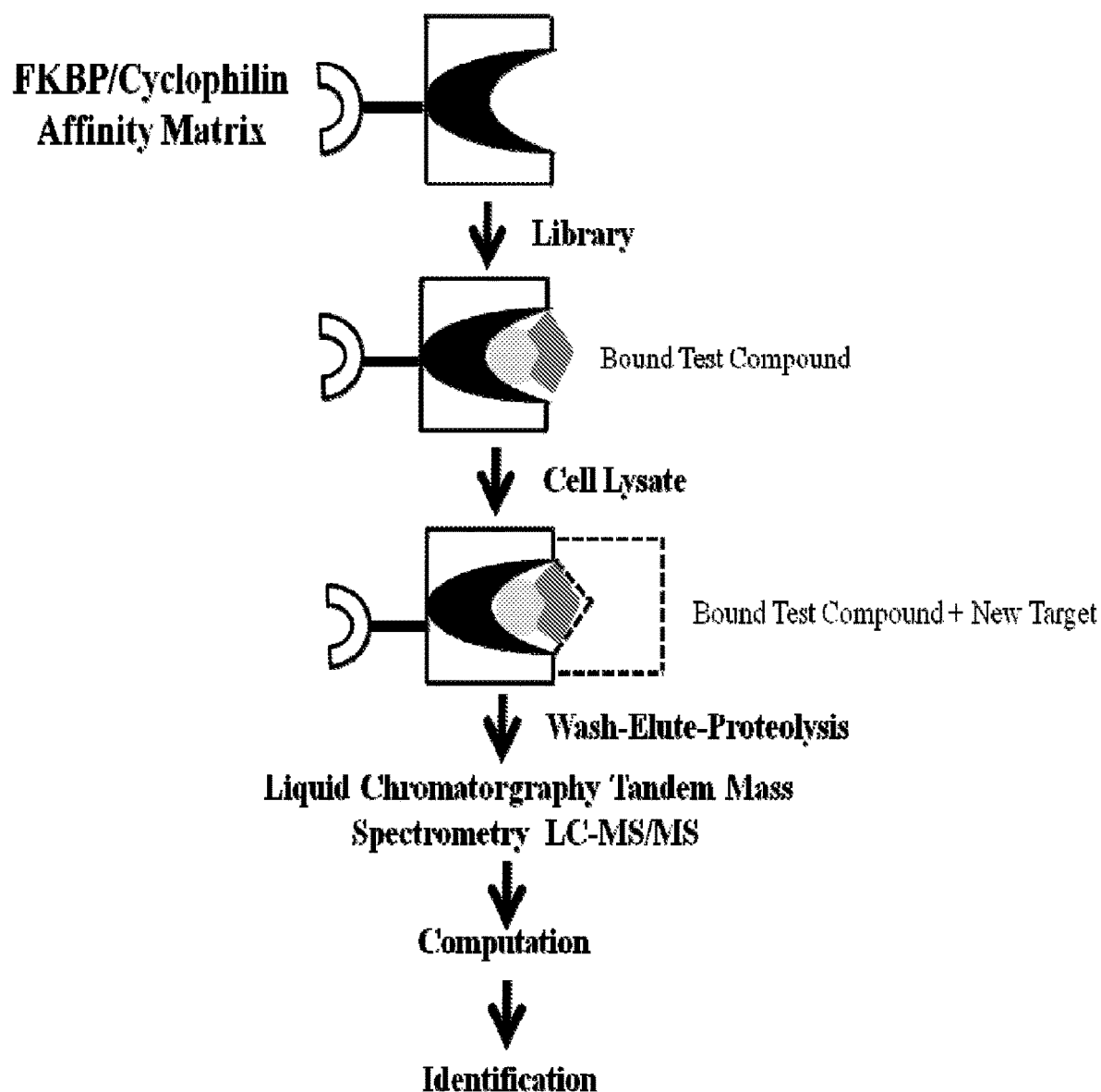
FIG. 2 is a schematic showing another representation of an affinity purification of protein complexes followed by mass spectrometric analysis allowing for target identification, using a FKBP/cyclophilin affinity matrix.

Unless otherwise indicated, the terms used herein are defined in the following paragraphs.

The term "halo" or "halogen" refers to any radical of fluorine, chlorine, bromine or iodine.

The term "alkyl" refers to a monovalent hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. In certain aspects, the term "alkyl" refers to a monovalent hydrocarbon chain that may be a straight chain or branched chain, containing 1 to 6 carbon atoms. In other aspects, the term "alkyl" refers to a monovalent hydrocarbon chain that may be a straight chain or branched chain, containing 1 to 4 carbon atoms.

The term "haloalkyl" refers to an alkyl in which one or more hydrogen atoms are replaced by halo, and includes alkyl moieties in which all hydrogens have been replaced by halo (e.g., perfluoroalkyl).

The term "alkenyl" refers to a monovalent straight or branched hydrocarbon chain containing 2-20 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. In certain aspects, the term "alkenyl" refers to a monovalent straight or branched hydrocarbon chain containing 2-6 carbon atoms and having one or more double bonds. In other aspects, the term "alkenyl"

refers to a monovalent straight or branched hydrocarbon chain containing 2-4 carbon atoms and having one or more double bonds.

The term "alkynyl" refers to a monovalent straight or branched hydrocarbon chain containing 2-20 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The terms "alkylamino" and "dialkylamino" refer to —NH(alkyl) and —NH(alkyl)$_2$ radicals respectively.

The term "aralkylamino" refers to a —NH(aralkyl) radical.

The term "alkylaminoalkyl" refers to a (alkyl)NH-alkyl-radical.

The term "dialkylaminoalkyl" refers to a (alkyl)$_2$N-alkyl-radical.

The term "mercapto" refers to an —SH radical.

The term "thioalkoxy" refers to an —S-alkyl radical.

The term "thioaryloxy" refers to an —S-aryl radical.

The term "alkoxy" refers to an —O-alkyl radical.

The term "aryl" refers to a monocyclic, bicyclic, or tricyclic aromatic hydrocarbon ring system. Examples of aryl moieties include, but are not limited to, phenyl, naphthyl, and anthracenyl.

The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "carbocyclyl" refers to a non-aromatic, monocyclic, bicyclic, or tricyclic hydrocarbon ring system. Carbocyclyl groups include fully saturated ring systems (e.g., cycloalkyls), and partially saturated ring systems.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). Examples of cycloalkyl moieties include, but are not limited to, cyclopropyl, cyclohexyl, methylcyclohexyl, adamantyl, and norbornyl.

The term "heteroaryl" refers to a fully aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms selected independently from N, O, or S if monocyclic, bicyclic, or tricyclic, respectively). Exemplary heteroaryl groups include (uranyl, imidazolyl, isoxazolyl, oxadiazolyl, oxazolyl, pyrazolyl, pyrrolyl, pyridyl, pyrimidinyl, pyridazinyl, thiazolyl, triazolyl, tetrazolyl, thienyl, pyrimidinyl, pyridinyl, pyridazinyl carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, or benzisoxazolyl.

The term "heterocyclyl" refers to a nonaromatic, 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The heteroatom may optionally be the point of attachment of the heterocyclyl substituent. Examples of heterocyclyl include, but are not limited to, tetrahydrofuranyl, tetrahydropyranyl, piperidinyl, morpholino, pyrrolinyl, pyrimidinyl, and pyrrolidinyl.

Bicyclic and tricyclic ring systems containing one or more heteroatoms and both aromatic and non-aromatic rings are considered to be heterocyclyl groups according to the present definition. Such bicyclic or tricyclic ring systems may be alternately characterized as being an aryl or a heteroaryl fused to a carbocyclyl or heterocyclyl, particularly in those instances where the ring bound to the rest of the molecule is required to be aromatic.

The terms "heteroarylalkyl" and "heteroaralkyl", as used herein, refers to an alkyl group substituted with a heteroaryl group.

The term "heterocyclylalkyl", as used herein, refers to an alkyl group substituted with a heterocyclyl group.

The term "acyl" refers to an alkylcarbonyl, cycloalkylcarbonyl, arylcarbonyl, heterocyclylcarbonyl, or heteroarylcarbonyl substituent, any of which may be further substituted (e.g., by one or more substituents).

Unless otherwise specified, an optionally substituted ring system (i.e, aryl, heteroaryl, carbocyclyl, cycloalkyl, heterocyclyl, etc.) or ring system portions of a group (e.g., the aryl portion of an aralkyl group) may be substituted at one or more substitutable carbon atoms with substituents independently selected from: halo, —C≡N, $C_1$-$C_4$ alkyl, =O, $C_3$-$C_7$ cycloalkyl, $C_1$-$C_4$ alkyl, —OH, —O—($C_1$-$C_4$ alkyl)-, —SH, —S—($C_1$-$C_4$-alkyl), —($C_1$-$C_4$—N($R^b$)($R^b$), —N($R^b$)($R^b$), —O—($C_1$-$C_4$ alkyl)-N($R^b$)($R^b$), —($C_1$-$C_4$ alkyl)-O—($C_1$-$C_4$ alkyl)-N($R^b$)($R^b$), —C(O)—N($R^b$)($R^b$), —($C_1$-$C_4$ alkyl)-C(O)—N($R^b$)($R^b$), —O-(heteroaryl), —O-(heterocycle), —O-phenyl, -heteroaryl, -heterocycle, and -phenyl, wherein:

each $R^b$ is independently selected from hydrogen, and —$C_1$-$C_4$ alkyl; or two $R^b$ are taken together with the nitrogen atom to which they are bound to form a 4- to 8-membered saturated heterocycle optionally comprising one additional heteroatom selected from N, S, S(=O), S(=O)$_2$, and O, any alkyl substituent is optionally further substituted with one or more of —OH, —O—($C_1$-$C_4$ alkyl), halo, —NH$_2$, —NH($C_1$-$C_4$ alkyl), or —N($C_1$-$C_4$ alkyl)$_2$; and any carbon atom on a phenyl, cycloalkyl, heteroaryl or heterocycle substituent is optionally further substituted with one or more of —($C_1$-$C_4$ alkyl), —($C_1$-$C_4$ fluoroalkyl), —OH, —O—($C_1$-$C_4$ alkyl), —O—($C_1$-$C_4$ fluoroalkyl), halo, —NH$_2$, —NH($C_1$-$C_4$ alkyl), or —N($C_1$-$C_4$ alkyl)$_2$;

Unless otherwise specified, all optionally substituted heterocyclyl ring systems (and any heterocyclyl substituents on any ring system) may be substituted on any substitutable nitrogen atom with —$C_1$-$C_4$ alkyl, or fluoro-substituted $C_1$-$C_4$ alkyl.

The term "substituted" refers to the replacement of a hydrogen atom by another group.

The term "oxo" refers to an oxygen atom, which forms a carbonyl when attached to carbon, an N-oxide when attached to nitrogen, and a sulfoxide or sulfone when attached to sulfur.

Many proteins function by binding to a large number of different partners. Many of these proteins adapt the inherent variability of the hot spot protein regions to present the same residues in different structural contexts. More specifically, the protein-protein interactions can be mediated by a class of natural products produced by a select group of fungal and bacterial species. These molecules, referred to herein as "naturally occurring Presentation Ligands", exhibit both a common structural organization and resultant functionality that provides the ability to modulate protein-protein interaction. These molecules contain a First Region that is highly conserved and a Second Region that exhibits a high degree of variability among the different naturally occurring Presentation Ligands. The constant region confers specificity for the presenter protein and allows a naturally occurring Presentation Ligand to bind to a presenter protein to form a binary complex; a variable region confers specificity for a target protein and allows a binary complex to bind to a target protein, typically modulating its activity.

Such naturally occurring Presentation Ligands are presented by presenter proteins, such as FKBPs and cyclophilins and act as diffusible, cell-penetrant, orally bio-available adaptors for protein-protein interactions. Examples include well known and clinically relevant molecules such as Rapamycin (Sirolimus), FK506 (Tacrolimus), and Cyclosporin. In brief, these molecules bind endogenous intracellular presenter proteins, the FKBPs e.g. rapamycin and FK506 or cyclophilins e.g. cyclosporin, and the resulting binary complexes of presenter protein-bound Presentation Ligand selectively bind and inhibit the activity of intracellular target proteins. Formation of a tripartite complex between the presenter protein, the Presentation Ligand and the target protein is driven by both protein-ligand and protein-protein interactions and both are required for inhibition of the targeted protein. In the example of the FKBP-rapamycin complex, the intracellular target is the serine-threonine kinase mTOR, whereas for FKBP-FK506 complex, the intracellular target is the phosphatase calcineurin. Of particular interest in the preceding two examples, FKBP12 is utilized as a partner presentation protein by both the rapamycin and FK506 presentation ligands. Moreover, the sub-structure components of rapamycin and FK506 responsible for binding to FKBP12 are closely related structurally, i.e. the so-called "Conserved Region," but it is the dramatic structural differences between rapamycin and FK506 in the non FKBP12-binding regions, i.e. the "Variable Region," that results in the specific targeting of two distinct intracellular proteins, mTOR and calcineurin, respectively. In this fashion, the Variable Regions of rapamycin and FK506 are serving as contributors to the binding energy necessary for enabling presenter protein-target protein interaction.

Disclosed herein are methods of identifying new biologically active agents having potential therapeutic utilities. These biologically active agents act in an analogous manner to naturally occurring Presentation Ligands by binding to presenter proteins, resulting in the formation of a binary complex that binds with high affinity to new target proteins, thereby modulating their activity. In some embodiments, biologically active agents identified by the disclosed assays "re-program" the binding of presenter proteins to protein targets that either do not normally bind to a presenter protein or greatly enhances binding affinity thereby resulting in the ability to modulate the activity of these new targets. As discussed above, naturally occurring Presentation Ligands contain a first region that is highly conserved (referred to herein as the "Presenter interacting Moiety" or "Conserved Region") and a second region of variability (referred to herein as the "Target Interacting Moiety" or "Variable Region"). A Presenter Interacting Moiety comprises one or more "Presenter interacting Sites" that mediate binding between the Test Compound and the presenter protein by making contacts with corresponding interacting sites on the presenter protein. A Target Interacting Moiety comprises one or more "Target Interacting Sites" that mediate binding between the Test Compound and the target protein by making contacts with corresponding interacting sites on the target protein.

Presentation Ligands bind to presenter proteins at the Conserved Region and, after formation of a binary complex with a presenter protein, bind to a target protein at the Variable Region. As such, a Target Interacting Moiety of a naturally occurring Presentation Ligand could be varied in many cases without significantly impairing the ability of a Presenter Interacting Moiety to bind to its presenter protein and form a binary complex. However, structural variation(s) in a Target interacting Moiety combined with binding of a Presenter Interacting Moiety of a naturally occurring Presentation Ligand to presenter protein can alter the binding specificity of the presenter protein/modified Presentation Ligand binary complex, allowing it to bind to and alter the activity of new target proteins.

The methods disclosed herein are directed to assays in which binary complexes are screened against therapeutic targets. Binary complexes comprise a presenter protein and an analog of a naturally occurring Presentation Ligand. New target proteins are selected for which a desirable therapeutic effect can be achieved through modulation of its biological activity. Structural analogues of a naturally occurring Presentation Ligand, referred to herein as "Test Compounds" are then prepared and/or selected. These structural analogues maintain the Conserved Region of the naturally occurring Presentation Ligand or, at most, contain insubstantial modifications that do not substantially impair binding to the presenter protein. Structural modifications, however, are made to the Target Interacting Moiety with the objective of reprogramming the binding specificity of a binary complex comprising the presenter protein and Test Compound. The presenter protein and the Test Compound are then combined under conditions suitable for formation of the binary complex, which is then screened for its ability to bind and/or modulate the activity of new target proteins.

Suitable presenter proteins for use in the disclosed assays are those which can bind a small molecule to form a binary complex, which can potentially bind to and modulate the activity of a target protein. In some embodiments, a presenter protein is one which is known to bind a Presentation Ligand to form a binary complex that is known to or suspected of binding to and modulating the biological activity of a target protein. Immunophilins are a class of presenter proteins which are known to have these functions and include FKBPs and cyclophilins.

In certain embodiments, a presenter protein is an immunophilin. In certain embodiments, a presenter protein is an immunophilin selected from the group consisting of FKBPs and cyclophilins. Exemplary FKBPs include FKBP12, FKBP12.6, FKBP13, FKBP19, FKBP22, FKBP23, FKBP25, FKBP36, FKBP38, FKBP51, FKBP52, FKBP60 and FKBP65, to name but a few. In some embodiments, a presenter protein is selected from the following table of FKBPs, which provides common names, an mRNA accession number, a protein accession number, structural information, peptidyl proline isomerase (PPI) activity, FK506 inhibition values, and rapamycin inhibition values.

| Name | Alias | mRNA accession # | Protein Accession # | Amino Acids | MW | PPI | FK506 Inhibition | Rapamycin Inhibition |
|---|---|---|---|---|---|---|---|---|
| FKBP12 | FKBP1A; FKBP12C | NM_000801.3; NM_054014.2 | P62942 | 108 | 12 | yes | 0.4 nM | 0.2 nM |
| FKBP12.6 | FKBP1B; FKBP9 | NM_004116.3; NM_054033.1 | P68106 | 108 | 12.6 | yes | 0.4 nM | 0.2 nM |
| FKBP13 | FKBP2 | NM_001135208.1 NM_004470.3 NM_057092.2 | P26885 | 142 | 13 | yes | 55 nM | 1.14 |
| FKBP19 | FKBP11 | NM_016594.1; NM_001143781.1 NM_001143782.1 | Q9NYL4 | 201 | 19 | yes | "weak" | nd |
| FKBP22 | FKBP14 | NM_017946.2 | Q9NWM8 | 211 | 22 | E. Inferred | Nd | nd |
| FKBP23 | FKBP7 | NM_001135212.1 | Q9Y680 | 259 | 23 | E. Inferred | Nd | nd |
| FKBP25 | FKBP3 | NM_002013.2; | Q00688 | 224 | 25 | yes | 160 nM | 0.9 nM |
| FKBP36 | FKBP6 | NM_001135211.1 NM_003602.3 | Q91XW8 | 327 | 36 | yes | 400 nM | 50 nM/0.9 nM |
| FKBP38 | FKBP8 | NM_012181.3 | Q14318 | 412 | 38 | yes | Nd | 500 nM |
| FKBP51 | FKBP54; FKBP5 | NM_001145775.1 NM_001145776.1 NM_001145777.1 NM_004117.3 | Q13451 | 457 | 51 | yes | yes, value not reported | 14.7 nM |
| FKBP52 | FKBP4; FKBP59 | NM_002014.3 | Q02790 | 459 | 59 | yes | 1 nM | 1.4 nM/6 nM |
| FKBP60 | FKBP9; FKBP63 | NM_007270; | O95302 | 507 | 63 | E. Inferred | nd | nd |
| FKBP65 | FKBP10 | NM_021939.2 | Q96AY3 | 582 | 65 | yes | 45 nM | 27-200 nM |

Terminology:
PPI: peptidyl proline isomerase activity; E. Inferred: electronically inferred; nd: not determined as inferred by public domain search.

Exemplary cyclophilins include Cyp-A, PPIL1, PPIL3, USA-Cyp, Cyp-F, Cyp-B, Cyp-C, Cyp29, Cyp33, Cyp40, SDCCAG10, Cyp57, Cyp60; HAL539, Cyp88, NK-Cyp, and RanBP2, to name but a few. In some embodiments, a presenter protein is selected from the following table of cyclophilins, which provides common names, an mRNA accession number, a protein accession number, structural information, PPI activity, and cyclosporine inhibition values.

| Name | Alias | mRNA accession # | Protein Accession # | Amino Acids | MW | PPI | Cyclosporin inhibition |
|---|---|---|---|---|---|---|---|
| Cyp-A | PP1A | NM_021130 | P62937 | 165 | 18 | yes | 6.8 nM |
| PPIL1 | CYPL1, PP1B, CGI-124, UNQ2425/ PRO4984 | NM_016059.4 | Q9Y3C6 | 166 | 19 | yes | 9.8 nM |
| PPIL3 | PPIL3; Cyclophilin J | NM_032472.3 | Q9H2H8-1; Q9H2H8-2 | 161 | 23 | nd | nd |
| USA-Cyp | CypH | NM_006347 | O43447 | 177 | 20 | yes | 160 nM |
| Cyp-F | Cyp3, PPIF | NM_005729 | P30405 | 207 | 22 | yes | 6.7 nM |
| Cyp-B | S-cyclophilin; SCYLP; CYP-S1 | NM_00942.2 | P23284 | 216 | 24 | yes | 8.4 nM |
| Cyp-C | PPIC | NM_000943 | P45877 | 212 | 23 | yes | 7.7 nm |
| Cyp29 | CAMLG; CAML | NM_001745 | P49069 | 296 | 33 | no | nd |
| Cyp33 | CypE | | Q9UNP9 | 331 | 34 | yes | 6.9 nM |
| Cyp40 | CypD; PPID | | Q08752 | 370 | 40 | yes | 61 nM |
| SDCCAG10 | CWC27; NY-CO-10 | NM_005869 | Q6UX04 | 472 | 54 | no | nd |
| Cyp57 | PPIL4 | NM_139126 | Q8WUA2 | 492 | 58 | nd | nd |
| Cyp60 | PPIL2 | NM_014337 | Q13356-1; Q1356-2 | 520 | 59 | no | no |
| HAL539 | Spliceosome- associated cyclophilin | NM_015342.2 | Q96BP3 | 646 | 74 | yes | 168 nM |
| Cyp88 | Cyp-G | NM_4792 | Q13427-1; Q13427-2 | 754 | 89 | yes | 51 nM |
| NK-Cyp | NK-TR protein | NM_005385 | P30414 | 1462 | 165 | yes | 488 nM |
| RanBP2 | NUP358 | NM_006267 | P49792 | 3224 | 360 | no | no |

Terminology:

PPI: peptidyl proline isomerase activity; Inferred: electronically inferred; nd: not determined as inferred by public domain search.

It will be appreciated that presentation proteins used in accordance with the present invention include allelic variants and splice variants of the FKBPs and cyclophilins recited above.

As with a naturally occurring Presentation Ligand, a Test Compound comprises a Presenter Interacting Moiety and a Target Interacting Moiety. In some embodiments, a Test Compound consists of a Presenter Interacting Moiety and a Target Interacting Moiety. Although a Test Compound can be linear, it is preferred that a Test Compound is cyclic, e.g., a macrocycle with at least ten ring atoms, and more commonly between 10 and 40 ring atoms, and even more commonly between 18 and 30 ring atoms. The ring atoms are typically selected from oxygen, nitrogen, carbon, sulfur and phosphorus and can unsubstituted or substituted and exist at various oxidation states.

In some embodiments, Presenter Interacting Sites and Target Interacting Sites are located in discrete regions of a macrocyclic ring structure, e.g., that do not overlap, which can be represented schematically as:

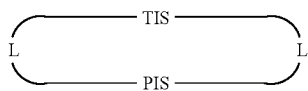

wherein "TIS" is a Target Interacting Site, "PIS" is a Presenter Interacting Site, and L is a bond or a bivalent substituted or unsubstituted portion of a macrocyclic chain.

In some embodiments, Presenter and Target Interacting Sites are connected to one another by a portion of a macrocyclic chain, which can be represented schematically as:

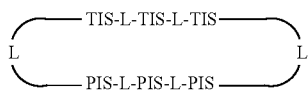

wherein "TIS" is a Target Interacting Site, "PIS" is a Presenter Interacting Site, and L is a bond or a bivalent substituted or unsubstituted portion of a macrocyclic chain.

In some embodiments, Presenter Interacting Sites and Target Interacting Sites are distributed on the Test Compound such that they interdigitate with one another, which can be represented schematically as:

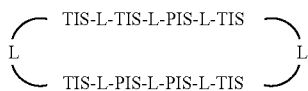

wherein "TIS" is a Target Interacting Site, "PIS" is a. Presenter Interacting Site, and L is a bond or a bivalent substituted or unsubstituted portion of a macrocyclic chain wherein each L is independently selected from a bond or a bivalent macrocyclic chain.

It will be appreciated that the preceding three schematics are representative structures that conceptually illustrate certain embodiments of the invention, and Test Compounds can have any number of Target Interacting Sites or Presenter Interacting Sites distributed throughout the compound.

When L is a bivalent macrocyclic chain, it should be understood that all or a portion of one or more bivalent macrocyclic chains may contribute to or enhance either a) the ability of the Presenter Interacting Moiety to bind to its respective Presenter Protein; and/or b) the ability of the Target interacting Moiety to interact with the Target Protein.

In some embodiments, and as disclosed earlier in U.S. Ser. No. 61/427,626, the Variable Region (or Target Interacting Moiety) is a portion of a macrocyclic ring structure. It will be appreciated that the Target Interacting Moiety may be varied in a multitude of ways including, but not limited to, modifications in the macrocyclic backbone and appendages to the macrocyclic backbone. In some embodiments, a Variable Region as described herein does not include the appendage of a complete known ligand via a linker to the macrocyclic backbone, wherein a "complete known ligand" is the entire chemical structure of a ligand that, by itself, is known to bind to a target protein.

In some embodiments, each bivalent macrocyclic chain is a linear chain of up to 10 atoms, independently selected from carbon, nitrogen, oxygen, sulfur or phosphorous atoms, wherein each atom in the chain is optionally substituted with one or more substituents independently selected from alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamide, cyano, oxo, thio, alkylthio, arylthio, acylthio, alkylsulfonate, arylsulfonate, phosphoryl, and sulfonyl, and wherein any two atoms in the chain may be taken together with the substituents bound thereto to form an optionally substituted carbocyclic, heterocyclic, aryl or heteroaryl ring, wherein the ring may be further optionally fused to one or more optionally substituted carbocyclic, heterocyclic, aryl or heteroaryl rings.

As discussed above, a Presenter Interacting Moiety is comprised of one or more Presenter interacting Sites. In some embodiments, one or more Presenter Interacting Sites is highly conserved among naturally occurring Presentation Ligands. In some embodiments, an entire Presenter interaction Moiety is highly conserved among naturally occurring Presentation Ligands. In some embodiments, such highly conserved Presenter Interacting Moieties and/or Presenter Interacting Sites allow a Test Compound to bind to a presenter protein, thereby forming a binary complex.

In one embodiment, a Presenter interacting Moiety binds to a FKBP and has the formula A:

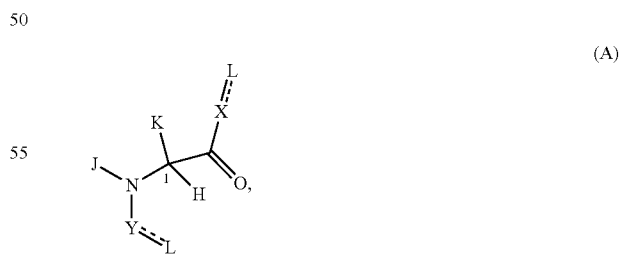

wherein:
J is hydrogen or (C1-C2) alkyl;
K is (C1-C4)-straight or branched alkyl, benzyl or cyclohexylmethyl; or
wherein J and K may be taken together to form a 5-7 membered heterocyclic ring which may contain an O, S, SO or $SO_2$ substituent therein;

the stereochemistry at carbon position 1 is R or S;

each L is independently selected from a bond and a linear chain of up to 10 atoms, independently selected from carbon, nitrogen, oxygen, sulfur or phosphorous atoms, wherein each atom in the chain is optionally substituted with one or more substituents independently selected from alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamide, cyano, oxo, thio, alkylthio, arylthio, acylthio, alkylsulfonate, arylsulfonate, phosphoryl, and sulfonyl, and wherein any two atoms in the chain may be taken together with the substituents bound thereto to form a ring, wherein the ring may be further substituted and/or fused to one or more optionally substituted carbocyclic, heterocyclic, aryl or heteroaryl rings;

X is selected from —NH—, —N(alkyl)-, —O—, —C(O)—, —CHOH—, —CH=, or —CH$_2$—;

Y is selected from —C(O)NH—, —(O)N(alkyl)-, —C(O)O—, —C(O)C(O)—, —C(O)CHOH—, —C(O)CH=, —C(O)CH$_2$—, and —S(O)$_2$;

===== represents a single or a double bond; and the points of attachment to the rest of the compound are through a terminus of each L.

In one embodiment of Formula A, Y is selected from —C(O)NH—, —(O)N(alkyl)-, —C(O)O—, —C(O)C(O)—, —C(O)CHOH—, —C(O)CH= and —C(O)CH$_2$—; and J and K are taken together to form a 5-7 membered heterocyclic ring of the formula:

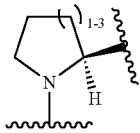

having the indicated stereochemistry, where the squiggly lines represent where the ring binds to the rest of the First Region.

Specific examples of Presenter interacting Moieties of Formula A, include the Conserved Region of FK506 shown below as Structural Formula I; and the Conserved Region of rapamycin and antascomicin shown below as Structural Formula II, where the points of attachment to the rest of the compound are represented by the squiggly lines.

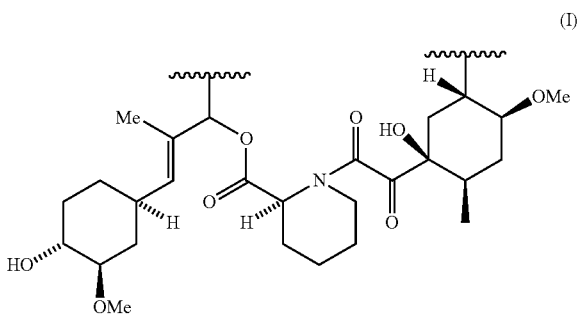

(I)

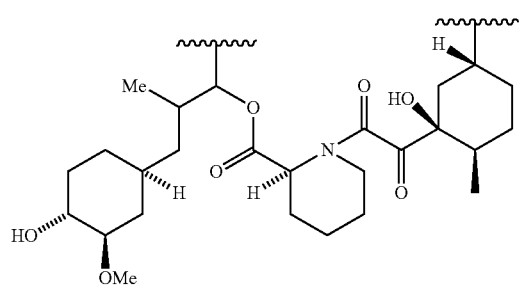

(II)

Another example of a Presenter Interacting Moiety of Formula A is the Conserved Region of certain rapamycin analogues see U.S. Pat. No. 7,276,498, the entire teachings of which are incorporated herein by reference) which is shown below as Structural Formula (III):

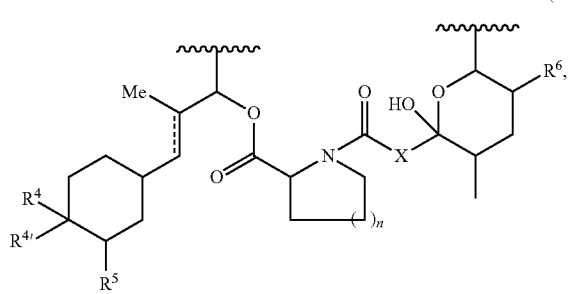

(III)

wherein $R^4$ and $R^{4'}$ are (a) independently selected from among H, OH, O($C_1$ to $C_6$ alkyl), O(substituted $C_1$ to $C_6$ alkyl), O(acyl), O(aryl), O(substituted aryl), and halogen; or (b) taken together to form a double bond to O; $R^5$ is selected from H, OH, and OCH$_3$; X is selected from —CH$_2$—, —CHOH— and C=O; $R^6$ is H or OCH$_3$; n is 1 or 2, and the points of attachment to the rest of the compound are represented by the squiggly lines. For Formula III, an aryl group is a $C_6$-$C_{10}$ carbocyclic aromatic group; and an acyl group is —CO($C_1$-$C_6$ alkyl).

Still other examples of a Presenter Interacting Moiety of Formula A are other groups which mimic the rapamycin Conserved Region and are represented below as Structural Formulas IV and V:

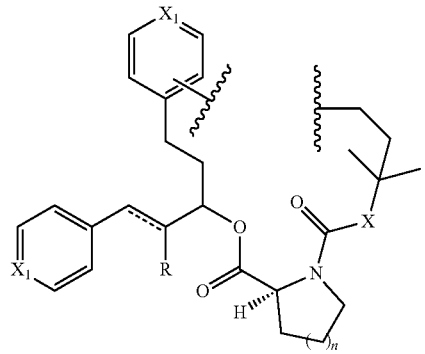

(IV)

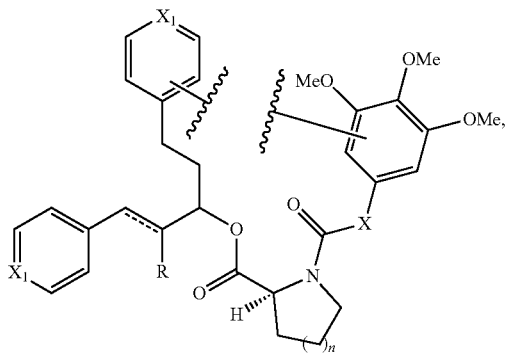

(V)

wherein each R is independently hydrogen or methyl, each $X_1$ is independently CH or N; X is C=O, CHOH or $CH_2$; n is 1 or 2, and the points of attachment to the rest of the compound are represented by the squiggly lines.

Still other examples of a Presenter Interacting Moiety of Formula A are other groups which can function as mimics of the rapamycin Conserved Region and are represented below as formula VI. Compounds represented by formula VI and their preparation are disclosed in U.S. Pat. No. 6,037,370, the entire teachings of which are incorporated herein by reference.

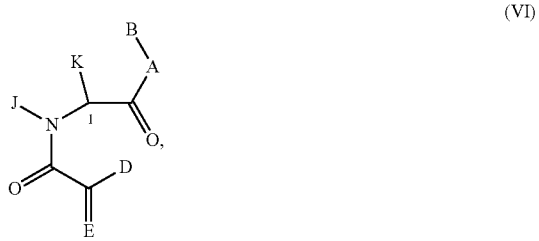

(VI)

wherein:

A is O, NH, or N—(C1-C4 alkyl);

B is CHL-Ar, (C1-C6)-alkyl, (C2-C6)-alkenyl, (C5-C7)-cycloalkyl, (C5-C7)-cycloalkenyl, Ar substituted (C1-C6)-alkyl, (C5-C7)-cycloalkenyl substituted (C2-C6)-alkenyl, Ar substituted(C2-C6)-alkenyl, or

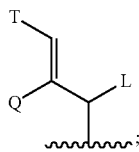

L and Q are independently hydrogen, (C1-C6-alkyl or (C2-C6)-alkenyl;

T is Ar or substituted cyclohexyl with substituents at positions 3 and 4 which are independently selected front the group consisting of hydrogen, hydroxyl, O—(C1-C4)-alkyl, O—(C2-C4)-alkenyl and carbonyl;

Ar is selected from the group consisting of 1-naphthyl, 2-naphthyl, 2-furyl, 3-furyl, 2-thienyl, 2-pyridyl, 3-pyridyl, 4-pyridyl and phenyl having one to three substituents which are independently selected from the group consisting of hydrogen, halo, hydroxyl, nitro, $CF_3$, (C1-C6)-alkyl, (C2-C6)-alkenyl, O—(C1-C4)-alkyl, O—(((C2-C4)-alkenyl), O-benzyl, O-phenyl, amino and phenyl;

D is hydrogen or U; E is either oxygen or CH-U, provided that if D is hydrogen, then E is CH-U or if E is oxygen then D is not hydrogen;

each U is independently selected from O—(C1-C4)-alkyl, O—((C2-C4)-alkenyl), (C1-C6)-alkyl, (C2-C6)-alkenyl, (C5-C7)-cycloalkyl, (C5-C7)-cycloalkenyl substituted with (C1-C4)-alkyl or (C2-C4)-alkenyl, 2-indolyl, 3-indolyl, (C2-C4)-alkenyl-Ar, or Ar; and J is hydrogen or (C1-C2) alkyl; K is (C1-$C_4$)-alkyl, benzyl or cyclohexylmethyl; or wherein J and K may be taken together to form a 5-7 membered heterocyclic ring which may contain an O, S, SO or $SO_2$ substituent therein;

the stereochemistry at carbon position 1 is R or S;

the points of attachment to the rest of the compound is by a covalent bond to a terminus of B and a covalent bond to a terminus of D.

More preferably for formula VI, A is oxygen; J is hydrogen or (C1-C2 alkyl); K is (C1-C4)-alkyl, benzyl or cyclohexylmethyl; or J and K are taken together to form pyrrolidyl or piperidyl; and the stereochemistry at carbon position 1 is S.

In the above preferred group wherein J and K are taken together to form pyrrolidyl or piperidyl and E is CH-U, U is preferably dimethylaminophenyl, methoxyphenyl, dimethoxyphenyl, trimethoxyphenyl, nitrophenyl, furyl, indolyl, pyridyl, or methylenedioxyphenyl.

In the above preferred groups wherein J and K are taken together to form pyrrolidyl or piperidyl and E is oxygen:

B is preferably benzyl, naphthyl, tert-butyl,

E-3-phenyl-2-methyl-prop-2-enyl, E-3-(4-hydroxyphenyl) 2-methyl-prop-2-enyl, E-3-[trans(4-hydroxycyclohexyl)]-2-methyl-prop-2-enyl, cyclohexylethyl, cyclohexylpropyl, cyclohexylbutyl, cyclopentylopropyl, E-3-(4-methoxyphenyl)-2-methyl-prop-2-enyl, E-3-(3,4-dimethoxyphenyl)-2-methyl-prop-2-enyl or E-3-[cis(4-hydroxycyclohexyl)]-2-methyl-prop-2-enyl; and D is preferably phenyl, methoxyphenyl, cyclohexyl, ethyl, methoxy, nitrobenzyl, thiophenyl, indolyl, furyl, pyridyl, pyridyl-N-oxide, nitrophenyl, fluorophenyl, trimethoxyphenyl or dimethoxyphenyl.

Yet other compounds of Structural Formula A, which can function as a Presenter Interacting Moiety are mimics of the rapamycin Conserved Regions are represented below as Formulas VII-VIII. Compounds represented by formulas VII-III and their preparation are disclosed in U.S. Pat. No. 6,037,370, the entire teachings of which are incorporated herein by reference.

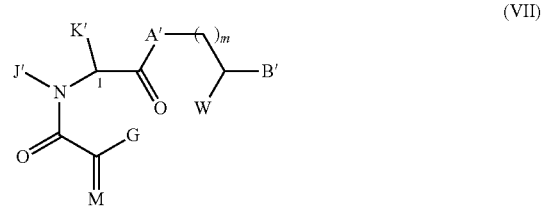

(VII)

-continued

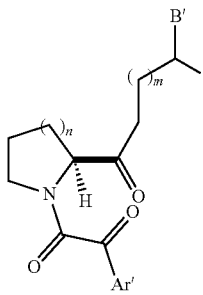
(VIII)

wherein

A' is CH$_2$, oxygen, NH or N—(C1-C4 alkyl);

B' and W are independently:

(i) (C1-C10)-alkyl, (C2-C10)-alkenyl, (C2-C10)-alkynyl, (C5-C7)-cycloalkyl substituted (C1-C6)-alkyl, (C5-C7)-cycloalkyl substituted (C2-C6)-alkenyl, (C5-C7)-cycloalkyl substituted (C2-C6)-alkynyl, (C5-C7)-cycloalkenyl substituted (C1-C6)-alkyl, (C5-C7)-cycloalkenyl substituted (C2-C6)-alkenyl, (C5-C7)-cycloalkenyl substituted (C2-C6)-alkynyl, Ar' substituted (C1-C6)-alkyl, Ar' substituted (C2-C6)-alkenyl, or Ar' substituted (C2-C6)-alkynyl wherein, in each case, any one of the CH$_2$ groups of said alkyl, alkenyl or alkynyl chains may be optionally replaced by a heteroatom selected from the group consisting of O, S, SO, SO$_2$, N, and NR, wherein R is selected from the group consisting of hydrogen, (C1-C4)-alkyl, (C2-C4)-alkenyl or alkynyl, and (C1-C4) bridging alkyl wherein a bridge is formed between the nitrogen and a carbon atom of said heteroatom-containing chain to form a ring, and wherein said ring is optionally fused to an Ar' group; or

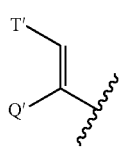
(ii)

wherein Q' is hydrogen, (C1-C6)-alkyl or (C2-C6)-alkenyl or alkynyl;

T' is Ar' or substituted 5-7 membered cycloalkyl with substituents at positions 3 and 4 which are independently selected from the group consisting of oxo, hydrogen, hydroxyl, O—(C1-C4)-alkyl, and O—(C2-C4)-alkenyl;

Ar' is a carbocyclic aromatic group selected from the group consisting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl phthalazinyl, quinazolinyl, quinoxalinyl, 1,8-naphthyridinyl, pteridinyl, carbazolyl, acridinyl, phenazinyl, phenothiazinyl, and phenoxazinyl;

Ar' may contain one to three substituents which are independently selected from the group consisting of hydrogen, halogen, hydroxyl, hydroxymethyl, nitro, trifluoromethyl, trifluoromethoxy, (C1-C6)-alkyl, (C2-C6)-alkenyl, O—(C1-C4)-alkyl, O—(C2-C4)-alkenyl, O-benzyl, O-phenyl, 1,2-methylenedioxy, amino, carboxyl, N—[(C1-C5)-alkyl or (C2-C5)-alkenyl)carboxamides, N,N-di-[(C1-C5)-alkyl or (C2-C5)-alkenyl)]carboxamides, N-morpholinocarboxamide, N-benzylcarboxamide, N-thiomorpholinocarboxamide, N-picolinoylcarboxamide, O—X, CH$_2$—(CH$_2$)$_q$—X, O—(CH$_2$)$_q$X, (CH$_2$)$_q$—O—X, and CH=CH—X;

X is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl;

q is 0-2;

G is hydrogen or U';

M is either oxygen or CH-U; provided that if G is hydrogen, then M is CH-U' or if M is oxygen, then G is U';

U° is O—[(C1-C4)-alkyl], O—[(C2-C4)-alkenyl], (C2-C6)-alkenyl, (C5-C7)-cycloalkyl, (C5-C7)-cycloalkenyl substituted with (C1-C4)-alkyl or (C2-C4)-alkenyl, (C2-C4)-alkenyl-Y or Y;

Y is selected from the group consisting of phenyl, 1-naphthyl, 2-naphthyl, indenyl, azulenyl, fluorenyl, anthracenyl, 2-pyrrolinyl, 3-pyrrolinyl, pyrolidinyl, 1,3-dioxolyl, imidazolidinyl, 2H-pyranyl, 4H-pyranyl, piperidyl, 1,4-dioxanyl, morpholinyl, thiomorpholinyl, piperazinyl, quinuclidinyl, and heterocyclic aromatic groups as defined for Ar' above;

Y may contain one to three substituents which are independently selected from the group consisting of hydrogen, halogen, hydroxyl, hydroxymethyl, nitro, trifluoromethyl, trifluoromethoxy, (C1-C6)-alkyl, (C2-C6)-alkenyl, O—(C1-C4)-alkyl, O—(C2-C4)-alkenyl, O-benzyl, O-phenyl, 1,2-methylenedioxy, amino, and carboxyl;

J' is hydrogen, (C1-C2) alkyl or benzyl;

K' is (C1-C4)-alkyl, benzyl or cyclohexylmethyl, or wherein J' and K may be taken together to form a 5-7 membered heterocyclic ring which may contain a heteroatom selected from the group consisting of O, S, SO and SO$_2$; and n is 1 or 2;

m is an integer from 0-10, preferably 0-3; and the points of attachment to the rest of the compound is by a covalent bond to a terminus of B' and a covalent bond to a terminus of G for Formula VII or a covalent bond to Ar' for formula VIII.

Preferably, B' and W are independently selected from:

Ar', (C1-C10)-alkyl, (C2-C10)-alkenyl, (C2-C10)-alkynyl, (C5-C7)-cycloalkyl substituted (C1-C6)-alkyl, (C5-C7)-cycloalkyl substituted (C2-C6)-alkenyl, (C5-C7)-cycloalkyl substituted (C2-C6)-alkynyl, (C5-C7)-cycloalkenyl substituted (C1-C6)-alkyl, (C5-C7)-cycloalkenyl substituted (C2-C6)-alkenyl, (C5-C7)-cycloalkenyl substituted (C2-C6)-alkynyl, Ar' substituted (C1-C6)-alkyl, Ar' substituted (C2-C6)-alkenyl or Ar' substituted (C2-C6)-alkynyl wherein, in each case, any one of the CH$_2$ groups of said alkyl, alkenyl or alkynyl chains may be optionally replaced by a heteroatom selected from the group consisting of O, S, SO, SO$_2$; or

(ii)

wherein any Ar' may contain one to three substituents which are independently selected from the group consisting of hydrogen, halogen, hydroxyl, hydroxymethyl, nitro, trifluoromethyl, trifluoromethoxy, (C1-C6)-alkyl, (C2-C6)-alkenyl, O—[(C1-C4)-alkyl], O—[(C2-C4)-alkenyl], O-benzyl, O-phenyl, 1,2-methylenedioxy, amino and carboxyl; and Y is selected from the group consisting of phenyl, 1-naphthyl, 2-naphthyl, indenyl, azulenyl, fluorenyl, anthracenyl and heterocyclic aromatic groups as defined for Ar' above.

In another preferred embodiment for Formula VII and VIII, at least one of B' or W is independently selected from the group consisting of (C2-C10)-alkynyl; (C5-C7)-cycloalkyl substituted (C2-C6)-alkynyl; (C5-C7)-cycloalkenyl substituted (C2-C6)-alkynyl; and Ar' substituted (C2-C6)-alkynyl.

Alternatively, at least one of B' or W is independently represented by the formula —$(CH_2)_r$—(Z)—$(CH_2)_s$Ar', wherein:

Z is independently selected from the group consisting of $CH_2$, O, S, SO, $SO_2$, N, and NR;

r is 0-4;

s is 0-1; and

Ar' and R are as defined above in formula VII.

In yet another alternative embodiment of formula VII or VIII, at least one of B' or W is independently selected from the group consisting of Ar', Ar'-substituted (C1-C6)-alkyl, Ar'-substituted (C2-C6)-alkenyl and Ar'-substituted (C2-C6)-alkynyl;

wherein Ar' is substituted with one to three substituents which are independently selected from the group consisting of N—((C1-C5)-alkyl or (C2-C5)-alkenyl) carboxamides, N,N-di-((C1-C5)-alkyl or (C2-C5)-alkenyl)carboxamides, N-morpholinocarboxamide, N-benzylcarboxamide, N-thiomorpholinocarboxamide, N-picolinoylcarboxamide, O—X, $CH_2$—$(CH_2)_q$—X, O—$(CH_2)_q$—X, $(CH_2)_q$O—X, and CH=CH—X; and Ar', X and q are as defined above.

Specific Conserved Regions are disclosed in U.S. Pat. No. 6,037,370 and are contemplated for use as First Regions in the disclosed methods.

Yet another embodiment of Formula A which can serve as a Presenter Interacting Moiety in the present invention is disclosed in U.S. Pat. No. 5,935,954 (the entire teachings of which are incorporated herein by reference) and represented by formula (IX):

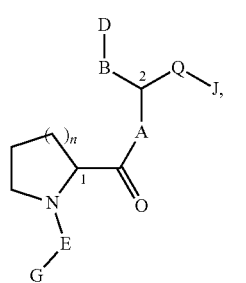

(IX)

wherein:

A is $CH_2$, O, NH or N—[(C1-C4)-alkyl];

B is (C1-C6)-alkyl, (C2-C6)-alkenyl or (C2-C6)-alkynyl, wherein one of the carbon atoms of B is optionally replaced by O, S, SO, $SO_2$, NH or N—[(C1-C4)-alkyl];

D is 1-[(C1-C4)-alkyl]-4-piperidinyl; 1-piperazinyl; 1-[(C1-C4)-alkyl]-4-piperazinyl; a 5-7-membered cycloalkyl or cycloalkenyl ring optionally comprising substituents at the 3 and/or 4 position of said ring, wherein said substituents are selected from oxo, OH, (C1-C4)-alkyl, O—(C1-C4)-alkyl, O—(C2-C4)-alkenyl, $NH_2$, N,N di-[(C1-C4)-alkyl] amino or halogen; or a monocyclic or bicyclic aromatic ring structure consisting of 5 to 6 members in each ring and optionally comprising up to 4 heteroatoms independently selected from N, O or S;

E is $SO_2$ or —C(O)—C(O)—;

G is 1-[(C1-C4)-alkyl]-4-piperidinyl, 1-piperazinyl, 1-[(C1-C4)-alkyl]-4-piperazinyl, (C1-C7)-alkyl, (C2-C7)-alkenyl, (C2-C7)-alkynyl, (C5-C7)-cycloalkyl, or a monocyclic or bicyclic aromatic ring structure consisting of 5 to 6 members in each ring; wherein up to two carbon atoms in any G are optionally and independently replaced by O, S, SO, $SO_2$ or N;

G optionally comprises up to three substituents independently selected from halogen, hydroxyl, (C1-C6)-alkyl, (C2-C6)-alkenyl, O—(C1-C5)-alkyl, O—(C2-C5)-alkenyl, O-benzyl, amino, carboxyl, N—[(C1-C5)-alkyl], N—[(C2-C5)-alkenyl], trifluoromethyl or trifluoromethoxy; and wherein one carbon atom of any individual substituent is optionally replaced by O, N or S;

Q is a five membered aromatic ring containing 1 to 2 heteroatoms selected from N, O or S, or a six membered aromatic ring containing 0 to 2 heteroatoms selected from N, O or S;

J is a monocyclic or bicyclic aromatic ring structure attached to the 3 position of Q consisting of 5 to 6 members in each ring, optionally comprising up to four heteroatoms independently selected from O, S, or N; and J optionally comprises up to 3 substituents independently selected from halo, OH, $CH_2$ OH, $NO_2$, $SO_3$ H, trifluoromethyl, trifluoromethoxy, O-phenyl, 1,2-methylenedioxy, $NR_1R_2$, amino, carboxyl, N—[(C1-C5)-alkyl]carboxamide; N—[(C2-C5)-alkenyl]-carboxamide, N-morpholinocarboxamide, N-benzylcarboxamide, N-thiomorpholinocarboxamide, N-picolinoylcarboxamide, morpholinyl, piperidinyl, O—$R_3$, $CH_2$—$(CH_2)_q$—$R_3$, O—$(CH_2)_q$—$R_3$, $(CH_2)_q$—O—$R_3$, CH=CH—$R_3$, (C1-C6)-alkyl, or (C2-C6)-alkenyl, wherein in any substituent one carbon atom is optionally replaced by a heteroatom selected from the group consisting of O, S, SO, $SO_2$, NH or N—[(C1-C4)-alkyl];

wherein $R_1$ and $R_2$ are independently selected from the group consisting of hydrogen, (C1-C6)-alkyl, (C2-C6)-alkenyl, (C2-C6)-alkynyl and benzyl;

$R_3$ is selected from the group consisting of 4-methoxyphenyl, 2-pyridyl, 3-pyridyl, 4-pyridyl, pyrazyl, quinolyl, 3,5-dimethylisoxazoyl, 2-methylthiazoyl, thiazoyl, 2-thienyl; 3-thienyl and pyrimidyl; and q is 0-2;

n is 1 or 2;

the stereochemistry at each of "1" and "2" is independently selected from (R) and (S); and the points of attachment to the rest of the compound is by a covalent bond to a terminus of J and a covalent bond to a terminus of G.

The "3 position of Q" recited above is relative to the point of attachment of Q to the rest of the compound. For the purposes of this application, this point of attachment is designated the 1 position, regardless of any potential conflict with accepted chemical nomenclature.

Another embodiment of Formula A which can serve as a Presenter Interacting Moiety in the present invention is also disclosed in U.S. Pat. No. 5,935,954 and is represented by formula (X):

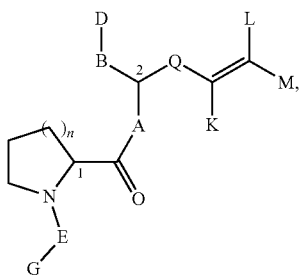

(X)

wherein:

A, B, D, E, G and Q are as defined as above for Formula IX;

K is H, (C5-C7) cycloalkyl, (C5-C6) aromatic ring, 1-[(C1-C4)-alkyl]-4-piperidinyl, 1-piperazinyl, 1-[(C1-C4)-alkyl]-4-piperazinyl, (C1-C7)-alkyl, (C2-C7)-alkenyl or (C2-C7)-alkynyl, wherein up to two carbon atoms in K are optionally replaced independently by O, S, SO, $SO_2$, NH, NO or N—(C1-C4)-alkyl, wherein K optionally comprises up to 2 substituents independently selected from halo, amino, hydroxy, carboxy, methoxy or (C1-C3)alkyl; and L and M are independently selected from H, (C1-C7)-alkyl, (C2-C7)-alkenyl or (C2-C7)-alkynyl, wherein one carbon atom in $R_2$ and $R_3$ is optionally replaced by O, S, SO, $SO_2$ NH or N—(C1-C4)-alkyl, wherein L and M optionally comprise up to two substituents independently selected from halogen, hydroxy, amino, carboxy, or a 5 to 6 membered aromatic ring, said aromatic ring comprising up to two heteroatoms selected from N, O or S;

n is 1 or 2;

the stereochemistry at each of "1" and "2" is independently selected from (R) and (S); and the points of attachment to the rest of the compound is by a covalent bond to a terminus of M and a covalent bond to a terminus of G.

Preferably, none of the monocyclic or bicyclic rings that may be present in either compounds of formulae (IX) or (X) contain more than one heteroatom per ring.

More preferably, in compounds of formulae (IX) and (X), A is oxygen and E is —C(O)—C(O)—. Even more preferred are compounds wherein n is 2 and the potential location of heteroatoms in Q exclude the 1 and 3 positions (i.e., the position where the aromatic ring is bound to the rest of the molecule and the position where i is bound to the aromatic ring). These compounds are represented by formulae (XI) and (XII):

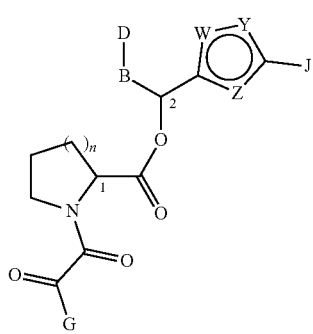

(XI)

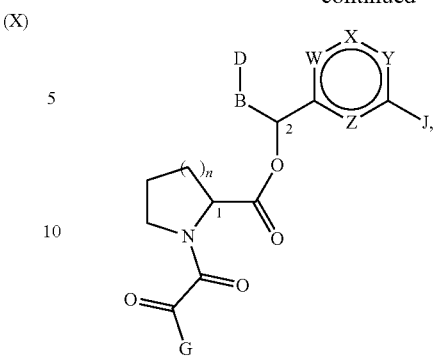

(XII)

wherein:

B is propyl, ethyl, or 1-methylethenyl;

D is phenyl, N-morpholinyl, 4-hydroxy-cyclohexyl, 4-(N-methyl)-piperidinyl, 4-pyridyl or pyranyl;

G is 3,4,5-trimethoxyphenyl, 3,4-dimethoxyphenyl, 4-fluorophenyl, 2-furanyl, 1,1-dimethyl-2-methoxyethyl, t-butyl, 4-(4-hydroxy) pyranyl, isobutyl, 4-pyranyl, isobutyl, isopropyl, 1-methylcyclohexyl, 1,1,2-trimethylpropyl, 1-hydroxycyclohexyl, 1-trimethylpropyl, 4-methoxy-1-hydroxycyclohexyl, 5-methoxymethyl-2-methylphenyl, 2-methylcyclohexyl, 5-(1-methyl-1-methoxyethyl)-2-methylcyclohexyl-2-enyl, 2-methylcyclohexyl, 5-(1-methyl-1-methoxyethyl)-2-methylcyclohexyl, 5-ethoxy-2-methylcyclohexyl, 4-ethoxy-N-aceto-2-pyrrolidinyl, or 5-isopropyl-2-methylcyclohexyl; and J is 4-phenyl-1-(3-pyridyl)-1-butenyl, 2,5-diethoxyphenyl, 4-phenyl-1-(3-pyridyl-N-oxide)-1-butenyl, 2-methoxyphenyl, 1-(3-pyridyl)-1-pentenyl, 2-ethoxyphenyl, 2,5-dipropoxyphenyl, 2,6-dimethoxyphenyl, 1-(3-pyridyl)-1-butenyl, 1-(3-pyridyl)-1-pentenyl, 1-(3-pyridyl)-1-hexenyl, 1-(4-methylphenyl)-1-pentenyl, 2,6-dimethoxymethylphenyl, 1-cyclohexyl-1-pentenyl, 2-ethoxymethyl-N-indolyl, 1-cyclohexyl-3-methoxy-1-propenyl, 2,6-diethoxymethylphenyl, 1-(3-pyridyl)-1-hexa-1,5-dienyl, 1-(4-pyranyl)-1-hexa-1,5-dienyl, 1-cyclohexyl-1-hexenyl, 2,5-dipropyl-N-pyrrolyl, 2-methyl-5-butyl-N-pyrrolyl, 3-(1-methoxy)-2-hexenyl, 3-(1-methoxy)-4-methyl-2-pentenyl, 2,5-dimethyl-N-pyrrolyl, 3-(2-methyl)-3-heptenyl or 2-(2-hexenyl);

W, X, Y and Z are independently selected from CH, N, O or S;

the stereochemistry at each of "1" and "2" is independently selected from (R) and (S); and the points of attachment to the rest of the compound is by a covalent bond to a terminus of J and a covalent bond to a terminus of G.

For formulas IX-XII, exemplary aromatic groups include phenyl, naphthyl, imidazolyl, isoxazolyl, oxadiazolyl, oxazolyl, pyrazolyl, pyrrolyl, pyridyl, pyrimidinyl, pyridazinyl, thiazolyl, triazolyl, tetrazolyl, thienyl, pyrimidinyl, pyridinyl, pyridazinyl, carbazolyl, benzimidazolyl, benzothienyl, benzofuranyl, benzotriazolyl, benzothiazolyl, benzoxazolyl, benzimidazolyl, isoquinolinyl, indolyl, isoindolyl, acridinyl, or benzisoxazolyl.

Individual compounds disclosed in U.S. Pat. No. 5,935,954 can also be used in the disclosed methods as Presenter Interacting Moieties of Formula A.

In another embodiment, a Presenter Interacting Moiety binds to a cyclophilin and is represented by Formula B:

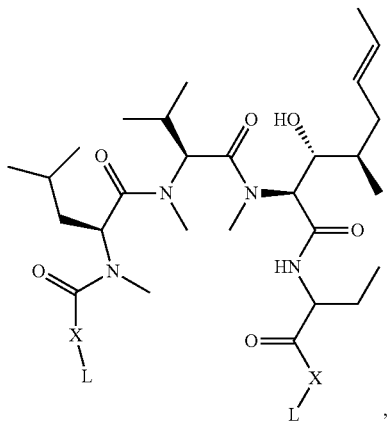

(B)

wherein each L is independently selected from a bond and a linear chain of up to 10 atoms, independently selected from carbon, nitrogen, oxygen, sulfur or phosphorous atoms, wherein each atom in the chain is optionally substituted with one or more substituents independently selected from alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, sulfonyl, and wherein any two atoms in the chain may be taken together with the substituents bound thereto to form a ring, wherein the ring may be further substituted and/or fused to one or more optionally substituted carbocyclic, heterocyclic, aryl or heteroaryl rings;

each X is independently selected from —NH—, —N(alkyl)-, —O—, —C(O)—, —CHOH—, or —CH$_2$—; and the points of attachment to the rest of the compound is by a covalent bond to a terminus of each L.

In a more specific embodiment of Formula C, a Presenter Interacting Moiety has the structure of the Conserved Region of cyclosporine represented by Structural Formula XIII:

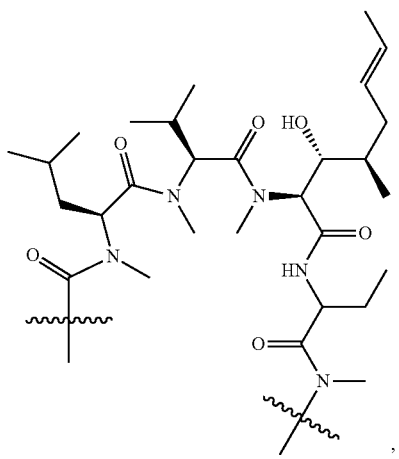

(XIII)

where the point of attachment to the rest of the compound is represented by the squiggly lines (see WO2010/034243, the entire teachings of which are incorporated herein by reference).

In another embodiment, a Presenter Interacting Moiety binds to a cyclophilin and is represented by Formula C:

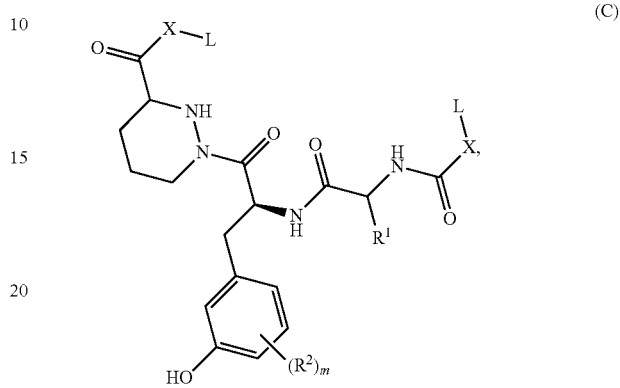

(C)

wherein

X and L are as defined for Formula (B);

R$^1$ is selected from (C1-C6)-alkyl, (C1-C6)-alkenyl, (C1-C6)-alkynyl, aryl, (C3-C7)-carbocyclyl, —(C1-C4 alkylene)-aryl, and —(C1-C4 alkylene)-(C3-C7 carbocyclyl;

each R$^2$ is independently selected from halo, —C≡N, C$_1$-C$_4$ alkyl, =O; C$_3$-C$_7$ cycloalkyl, C$_1$-C$_4$ alkyl, —OH, —O—(C$_1$-C$_4$ alkyl)-, —SH, —S—(C$_1$-C$_4$ alkyl), —(C$_1$-C$_4$ alkyl)-N(R$^b$)(R$^b$), —N(R$^b$)(R$^b$), —O—(C$_1$-C$_4$ alkyl)-N(R$^b$)(R$^b$), —(C$_1$-C$_4$ alkyl)-O—(C$_1$-C$_4$ alkyl)-N(R$^b$)(R$^b$), —C(O)—N(R$^b$)(R$^b$), —(C$_1$-C$_4$ alkyl)-C(O)—N(R$^b$)(R$^b$), —O-(heteroaryl), —O-(heterocycle), —O-phenyl, -heteroaryl, -heterocycle, and -phenyl, wherein:

each R$^b$ is independently selected from hydrogen, and —C$_1$-C$_4$ alkyl; or two R$^b$ are taken together with the nitrogen atom to which they are bound to form a 4- to 8-membered saturated heterocycle optionally comprising one additional heteroatom selected from N, S, S(=O), S(=O)$_2$, and O, any alkyl substituent is optionally further substituted with one or more of —OH, —O—(C$_1$-C$_4$ alkyl), halo, —NH$_2$, —NH(C$_1$-C$_4$ alkyl), or —N(C$_1$-C$_4$ alkyl)$_2$; and any carbon atom on a phenyl, cycloalkyl, heteroaryl or heterocycle substituent is optionally further substituted with one or more of —(C$_1$-C$_4$ alkyl), —(C$_1$-C$_4$ fluoroalkyl), —OH, —O—(C$_1$-C$_4$ alkyl), —O—(C$_1$-C$_4$ fluoroalkyl), halo, —NH$_2$, —NH(C$_1$-C$_4$ alkyl), or —N(C$_1$-C$_4$ alkyl)$_2$;

m is 0, 1, 2 or 3; and the points of attachment to the rest of the compound is by a covalent bond to a terminus of each L.

In a more specific embodiment of Formula C, a Presenter interacting Moiety has the structure of the Conserved Region of sanglifehrin represented by Structural Formula XIV (see WO2010/034243):

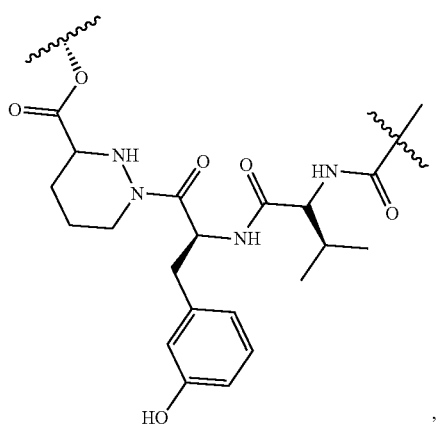

(XIV)

wherein the points of attachment to the rest of the molecule are represented by the squiggly lines.

In certain embodiments, structural modifications can be made to formulas provided that they do not substantially reduce the ability of a Presenter Interacting Moiety to form a complex with a presenter protein e.g., reduce binding by more than 5%, 10%, 15%, 20%, 25%, or 30%. In certain embodiments, structural modifications can be made to formulas I-XIV, provided that they do not substantially reduce the ability of a Presenter Interacting Moiety to form a complex with an immunophilin, such as an FKBP or cyclophilin, by more than 5%, 10%, 15%, 20%, 25%, or 30%. Reduction in binding between the Presenter Interacting Moiety and presenter proteins can be determined by methods well known in the art, e.g., as described below in the subsequent paragraphs.

The Target interacting Moiety, also referred to herein as the "Variable Region", is for enhancing the affinity of the binary complex for a target relative to the affinity of a presenter protein alone (without the binary complex) or a Test Compound alone (without the binary complex). In some embodiments, a presenter protein alone and/or a Test Compound alone will have no affinity (i.e., does not bind) for a target protein. In these instances, enhancement of affinity of a binary complex for a target protein can be assessed merely by determining using methods known in the art, e.g., by mass spectrometry based proteomic strategy (e.g., for example Liang et al., *Current Proteomics* 6:25 (2009) and Bauer and Kunster *Eur. J. Biochem.* 270:570 (2003), the entire teachings of which are incorporated herein by reference), whether a ternary complex of a presenter protein, Test Compound, and target protein formed. Alternatively, where there is some affinity between a target protein and a presenter protein and/or Test Compound, the actual binding affinities of each complex are measured by methods known in the art. For example, to ascertain whether affinity of a binary complex for a target protein is increased relative to either the affinity of a compound for a target protein in the absence of a binary complex or affinity of a presenter protein in the absence of a binary complex, requires calculation of the dissociation constant ($K_d$). The $K_d$ is a specific type of equilibrium constant that measures the propensity of a larger object to separate (dissociate) reversibly into smaller components, as when a complex falls apart into its component molecules. For example, the ($K_d$) describes the affinity between a ligand (L) (such as a drug) and a protein (P) i.e. how tightly a ligand binds to a particular protein.

There are multiple established technical methods to calculate $K_d$ (reviewed in Stockwell, B. R. Nature; 432 (7019): 846-54 (2004)) and have applicability to generate data to address questions as highlighted above. Specific techniques such as Surface Plasmon Resonance (SPR) and Fluorescence Polarization (FP) may represent preferred but not exclusive methodologies for calculating $K_d$. SPR measures the change in refractivity of a metal surface when a compound binds to a protein that is immobilized on that metal surface (Homola, J., Annal. Bioanal, Chem.; 377: 528-539 (2003)) while FP measures the change in tumbling rate for a compound when it is bound to a protein using loss-of-polarization of incident light (Burke, T. J., et. al. Comb. Chem. High Throughput Screen; 6: 183-194 (2003)). Each of these technologies has proven amenable to calculating the $K_d$ of protein-drug-protein complexes (Banaszynski, L. A. et. al. J. Am. Chem. Soc.; 127: 4715-4721 (2005)) and thus provides means to determine whether the affinity of the aforementioned binary complex for the target protein is increased relative to either the affinity of the compound for the target protein in the absence of the binary complex or affinity of the presenter protein in the absence of the binary complex.

In some embodiments, binding affinity is assessed by measuring whether a biological activity of a target protein is modulated by a binary complex. In some embodiments, the Variable Region of a macrocylic compound is bivalent, i.e., has two ends, each of which covalently binds to an end of the Conserved Region. This is depicted structurally below in Structural Formulas A1, B1, C1 and Ia-XIVa:

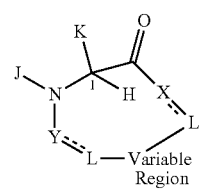

(A1)

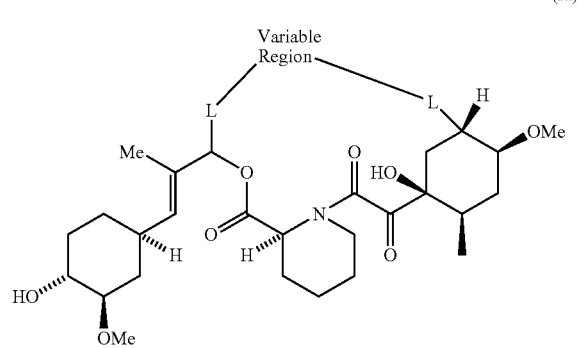

(Ia)

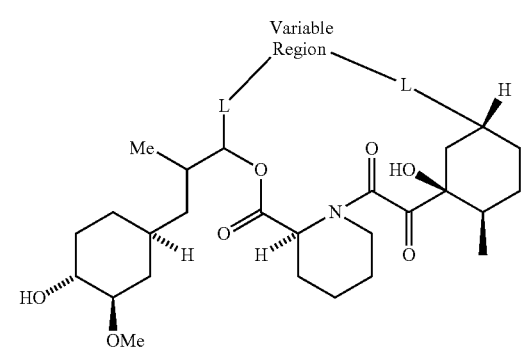
(IIa)
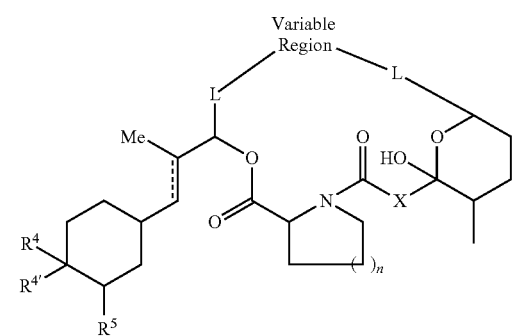
(IIIa)
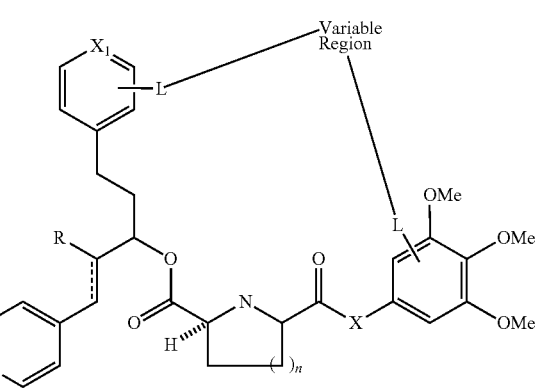
(IVa)
(Va)
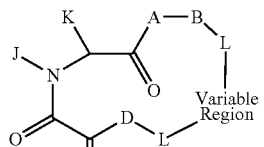
(VIa)
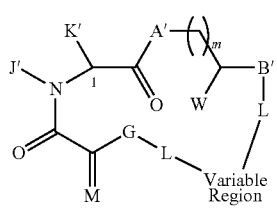
(VIIa)
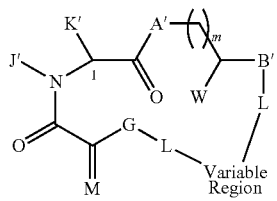
(VIIIa)
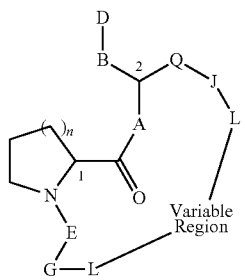
(IXa)
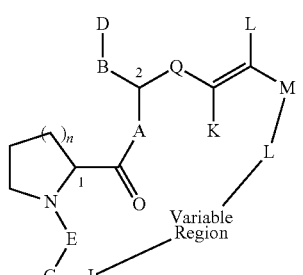
(Xa)
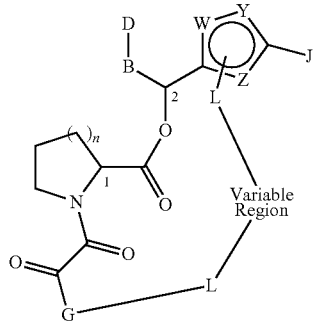
(XIa)

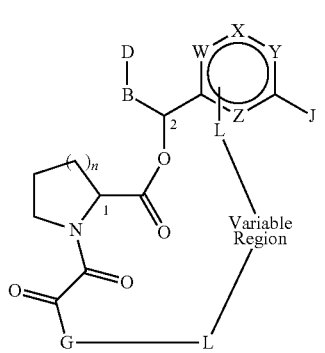

(B1)

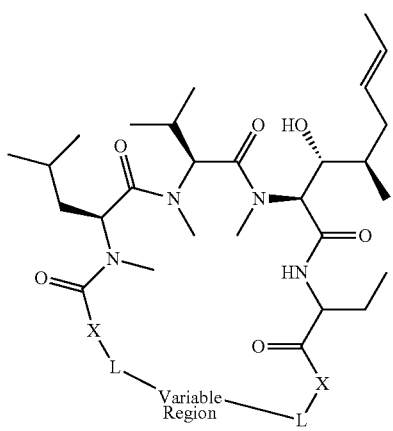

(XIIIa)

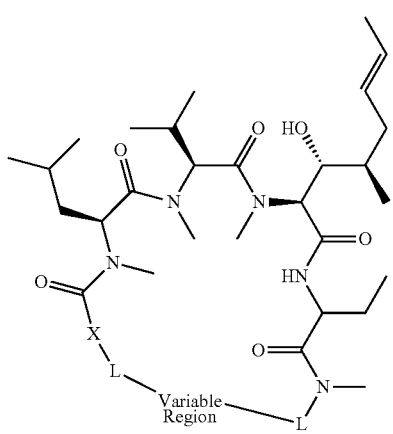

(C1)

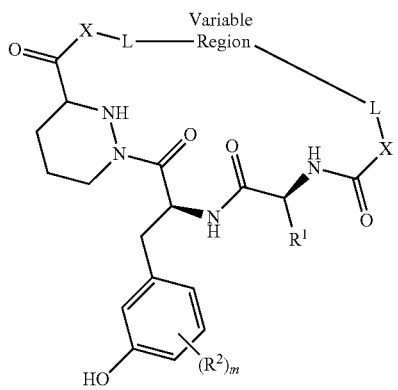

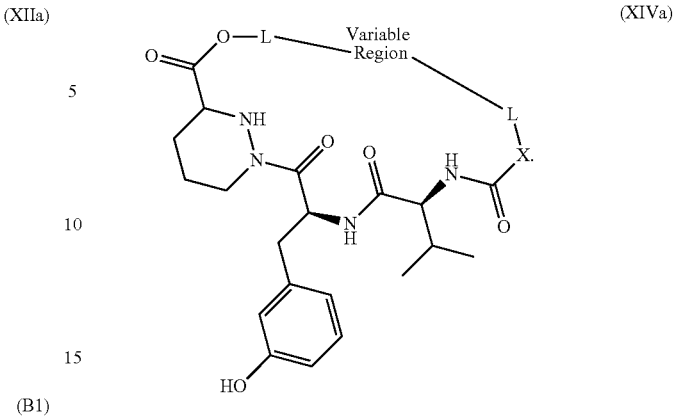

(XIIa)

(XIVa)

The variables in Structural Formulas A1, B1, C1 and Ia through XIVa are as defined above and described in classes and subclasses herein (e.g., corresponding Structural Formulas A, B, C and I-XIV).

In some embodiments, a Variable Region is a linear bivalent C4 to C30 (preferably C6-C20, more preferably C6-C15) aliphatic group consisting of carbon and hydrogen, optionally comprising one or double bonds. One or more of the carbon atoms in the aliphatic group can be optionally replaced with a functional group selected from O, S, SO, $SO_2$, CO, COO, OCO, $CONR^2$, $OCONR^2$, $NR^2$, $SO_2NR^2$, $NR^2CONR^2$ and $NR^2SO_2NR^2$. The functional group can be bidirectional (e.g., $CONR^2$ and $NR^2CO$ are both included) and $R^2$ is hydrogen or an alkyl group optionally substituted with one or more groups selected from —CN, —$NO_2$, —$OR^c$, —$NR^aR^b$, —$S(O)_iR^c$, —$NR^dS(O)_iR^c$, —$S(O)_iNR^eR^f$, —$C(=O)OR^c$, —$OC(=O)OR^c$, —$C(=S)OR^c$, —$O(C=S)R^c$, —$C(=O)NR^eR^f$, —$NR^dC(=O)R^c$, —$C(=S)NR^eR^f$, —$NR^dC(=S)R^c$, —$NR^d(C=O)OR^c$, —$O(C=O)NR^eR^f$, —$NR^d(C=S)OR^c$, —$O(C=S)NR^eR^f$, —$NR^d(C=O)NR^eR^f$, —$NR^d(C=S)NR^eR^f$, —$C(=S)R^c$ and —$C(=O)R^c$; $R^a$ and $R^b$ are each independently —H or $(C_1-C_6)$alkyl optionally substituted with 1 to 3 substituents independently selected from the group consisting of halogen, hydroxy, —$NR^gR^h$ and $(C_1-C_3)$alkoxy; $R^c$ is —H, or $(C_1-C_6)$alkyl optionally substituted with 1 to 3 substituents independently selected from the group consisting of halogen, hydroxy and $(C_1-C_3)$alkoxy; $R^d$ is —H or $(C_1-C_6)$alkyl optionally substituted with 1 to 3 substituents independently selected from the group consisting of halogen, hydroxy and $(C_1-C_3)$alkoxy; $R^e$ and $R^f$ are each independently —H or $(C_1-C_6)$alkyl optionally substituted with 1 to 3 substituents independently selected from the group consisting of halogen, hydroxy and $(C_1-C_3)$alkoxy; and $R^g$ and $R^h$ are each independently selected from the group consisting of —H, $(C_1-C_6)$alkyl, halo$(C_1-C_6)$alkyl, hydroxy$(C_1-C_6)$alkyl and $(C_1-C_3)$alkoxy$(C_1-C_6)$alkyl. Each carbon atom in the aliphatic group is optionally substituted with —CN, —$NO_2$, —$OR^c$, —$NR^aR^b$, —$S(O)_iR^c$, —$NR^dS(O)_iR^c$, —$S(O)_iNR^eR^f$, $C(=O)OR^c$, —$OC(=O)OR^c$, —$C(=S)OR^c$, —$O(C=S)R^c$, —$C(=O)NR^eR^f$, —$NR^dC(=O)R^c$, —$C(=S)NR^eR^f$, —$NR^dC(=S)R^c$, —$NR^d(C=O)OR^c$, —$O(C=O)NR^eR^f$, —$NR^d(C=S)OR^c$, —$O(C=S)NR^eR^f$, —$NR^d(C=O)NR^eR^f$, —$NR^d(C=S)NR^eR^f$, —$C(=S)R^c$ and —$C(=O)R^c$. The bivalent aliphatic group can also be substituted with a targeting group that mimics a ligand that binds to a target protein, wherein the targeting group is less than the ligand known to bind a target protein. In other words, a targeting group is a truncated portion or a fragment of a ligand. In some embodiments, a targeting group is a pharmacophore of a ligand. In some embodiments, a targeting group is a fragment of a pharmacophore of a ligand. Examples of such targeting groups include phosphotyrosine mimetics, ATP mimetics, and the like. While not wishing to be bound by any particular theory, it is believed that a truncated portion or fragment of a ligand will form some contacts that contribute to the binding energy enabling presenter protein-target protein interaction, but that additional contacts between the target protein and one or more ring atoms in the Variable Region will also contribute to the binding energy. In some embodiments, a targeting group is one of multiple Target Interacting Sites in a Target Interacting Moiety. Additional contacts between the target protein and presenter protein may also contribute to the binding energy of the presenter protein-target protein interaction.

In some embodiments, a Test Compound is a macrocycle and a target protein binds to a ring atom in the Variable Region (i.e., a ring atom of a Target Interacting Moiety). In some embodiments, a target protein binds to two or more ring atoms in a Variable Region. In some embodiments, a target protein binds to a substituent attached to one or more ring atoms in a Variable Region. In some embodiments, a target protein binds to one or more ring atoms in the Variable Region and to a substituent attached to one or more ring atoms in a Variable Region. In certain embodiments, a target protein binds to a group that mimics a ligand of a target protein and wherein the group that mimics a ligand of a target protein is attached to a Variable Region. In certain embodiments, a target protein binds to a presenter protein and the affinity of a target protein for a presenter protein in a binary complex is increased relative to the affinity of a target protein for a presenter protein in the absence of the complex. In some embodiments, binding in the preceding examples is through non-covalent interactions of a target protein to a Variable Region.

A target protein is a protein which mediates a disease condition or a symptom of a disease condition. As such, a desirable therapeutic effect can be achieved by modulating (inhibiting or increasing) its activity. Such desireable therapeutic effects include those where the activity of a target protein is measured directly or indirectly (e.g., where modulating the target protein has a measureable effect on a downstream process, substrate, activity, etc., which is more easily measured and/or observed). In some embodiments, target proteins which are tested in an assay are those which do not naturally associate with a presenter protein, e.g., those which have an affinity for a presenter protein in the absence of a binary complex with a Presentation Ligand of greater than 1 µM, preferably greater than 5 µM and more preferably greater than 10 µM. In some embodiments, target proteins which do not naturally associate with a presenter protein are those which have an affinity for a Test Compound in the absence of a binary complex with a Presentation Ligand of greater than 1 µM, preferably greater than 5 µM and more preferably greater than 10 µM. In certain embodiments, target proteins which do not naturally associate with a presenter protein are those which have an affinity for a binary complex of cyclosporine, rapamycin, or FK506 and a presenter protein (e.g., FKBP) of greater than 1 µM, preferably greater than 5 µM and more preferably greater than 10 µM. In some embodiments, target proteins which do not naturally associate with a presenter protein are those which are other than calcineurin or mTOR.

The selection of suitable target proteins for the disclosed assays may depend on a presenter protein. For example, target proteins that have low affinity for a cyclophilin may have high affinity for an FKBP and would not be used together with the latter. Target proteins can be naturally occurring, e.g., wild type. In some embodiments, a target protein can vary from a wild type protein but still retain biological function, e.g., as an allelic variant, a splice mutant or a biologically active fragment. In certain embodiments, a target protein is selected from the group consisting of K-Ras, N-Ras, H-Ras, c-Raf, c-Myc, N-Myc, L-Myc, beta-catenin, MITF, Hif-1alpha, Hif-2alpha, PKN3, Bcl6, E2F1, AAC-11, PCSK 9, EIF4E, PLD1, PLD2, AAC-11, Frizzled7, c-Src, Fak, RaLP, Pyk2, NF-kappaB, MLL-1, Myb, Ezh2, Stat3, Stat5, c-Fos, C-Jun, RhoGD12, AMPK, EGFR CTLA4, Rab25, Rab11, AR(coact), ER(coact), GCGC (coact), Adiponectin R2, GPR 81, and IMPDH2. In some embodiments, a target protein is selected from the group consisting of IL-4R, IL-13R, IL-1R, IL2-R, IL-6R, IL-22R TNF-R, TLR4, Nrlp3, TRKB, STEP, OTR, Tau, and Nav1.7

In some embodiments of a provided method, a Test Compound is contacted with a presenter protein under conditions suitable for the formation of a binary complex. In some embodiments, a Test Compound comprises a Presenter Interacting Moiety that is known to bind to the presenter protein being utilized in the assay. In such cases, conditions for forming such binary complexes are known to the skilled person. Suitable conditions for Test Compounds comprising a rapamycin Presenter Interacting Moiety can be found in Bierer, B. E., Mattila, P. S., Standaert, R. F., Herzenberg, L. A., Burakoff, S. J., Crabtree, G. & Schreiber, S. L. *Proc. Natl. Acad. Sci.* USA 87, 9231-9235 (1990); suitable conditions for Test Compounds comprising an FK506 Presenter Interacting Moiety can be found in Harding M W, Galat A, Uehling D E, Schreiber S. L. *Nature;* 341(6244):758-60 (1989); suitable conditions for Test Compounds comprising an cyclosporine Presenter Interacting Moiety can be found in Handschumacher R E, Harding N M, Rice J, Drugge R J, Speicher D W Science; 226(4674):544-7 (1984); and suitable conditions for Test Compounds comprising a sanglifehrin Presenter Interacting Moiety can be found in WO2010/034243. The entire teachings of these references are incorporated herein by reference. Suitable conditions for compounds comprising a Presenter Interacting Moiety which varies structurally from those listed above can be determined through routine variation of binding conditions for known Presentation Ligands.

Once a binary complex has formed, it is contacted with a target protein or target proteins. Target proteins can be in a purified form and simply added to an assay. In some embodiments, a binary complex is contacted with cell lysates containing target proteins of interest. In some embodiments, cell lysates are of neuronal origin, cardiac origin, or myeloid origin, or are lysates of cancer cell lines or lymphoid tissue. In some embodiments, cell lysates are from microorganisms. In some embodiments, cell lysates are from primary cells. In some embodiments, cell lysates are derived from any cell having an immunophilin or cyclophilin. The contacting is conducted under conditions known to form ternary complexes between presenter protein, Presentation Ligands and target proteins, e.g., as taught in Liu J, Farmer J D Jr, Lane W S, Friedman J, Weissman I, Schreiber S L. Cell. 1991 Aug. 23; 66(4):807-15; Vogel K et al Advances in Protein Chemistry Volume 56, 2001, Pages 253-291.

After contacting a binary complex with a target protein, the mixture is assessed to determine the affinity of the binary complex for the target protein is increased relative to either the (i) affinity of a compound for a target protein in the absence of the binary complex; or (ii) the affinity of a presenter protein for a target protein in the absence of the binary complex. Where a target protein is known to not substantially bind to a presenter protein or Test Compound in the absence of the binary complex, identification of a ternary complex is indicative of an increase in affinity. Binding can be determined by any suitable means, as discussed above. A preferred means is by tandem mass spectrometry. Where there is detectable binding between a target protein and a Test Compound or presenter protein, affinities of resulting complexes are measured, as discussed above.

One common way of carrying out a provided assay is by affinity purification of protein complexes followed by mass spectrometric analysis. As described below, this approach can be deployed to evaluate libraries of small molecule ligands for their ability to enable novel protein-protein interactions. In brief, "the bait", an epitope tagged version of a presenter protein e.g. the human FKBP or cyclophilin protein can be generated and used to "fish" for ligand-mediated protein-protein events. The bound proteins can then be identified by proteolytic digestion, analytical analysis by liquid chromatography-tandem mass spectrometry and computational search algorithms to identify the peptides and their constituent proteins (see the Figure).

It will be appreciated that a variety of methods can be used to analyze the influence of small molecules on protein-protein intereactions. For example, one basic procedure for generating an affinity column is to append a cDNA of interest (human immunophilins/FKBPs or cyclophilins with an epitope tag consisting of a polypeptide added to the N- or C-terminus of the cDNA open reading frame. This modified cDNA in an appropriate expression vector is then introduced into a suitable host e.g. a mammalian cell line or bacterial strain, at which time the cDNA is transcribed and translated by the cellular machinery to generate the epitope tagged recombinant protein. The cells can be lysed under appropriate non-denaturing conditions by a number of methods including sonication, French press, bead milling, treatment with lytic enzymes (e.g., lysozyme) or use of a commercially available cell lysis reagent such as the FastBreak™ Cell Lysis Reagent (Promega Inc.). Affinity capture purification is then performed following a procedure that is based on the affinity properties of the tag (Nilsson, J. et al Protein Expr Purif. 11(1):1-16, (1997)). Many different affinity tags have been developed to simplify protein purification including poly-histidine, DDK, Glutathione-S-Transferase-glutathione (GST-GSH), Hemagluttin (HA), and others (Terpe, K. Appl Microbiol Biotechnol., Appl Microbiol Biotechnol., 60(5):523-33 (2003). In brief, this affinity tagged bait protein is first purified from its production source (bacterial cells, mammalian cells, etc.) and then added to cell lysate generated from an organisms or source of interest (e.g. Human cell lines, etc,) resulting in a mixture to which compounds can either be added or not. After incubation for sufficient time as to allow for protein complex formation (i.e., Presenter-compound-target(s)), the bait protein and associated proteins are purified using the strategy appropriate for the epitope tag of the bait (presenter) protein. These purified proteins are then digested into peptides (either on column or after elution using appropriate methods) using a suitable proteinase (Trypsin, Endoproteinase Lys-C, etc.) and this resulting peptide mixture is the material that will be analyzed using mass spectrometry methodologies (tandem mass spectrometry, MS3 methods, etc.). Below is described one example of how such a process could be used for identification of target proteins for a bait (presenter) protein of interest wherein the bait protein is fused at its amino terminus to GS, however, appropriate modifications to this described methodology would be adopted if other putification tags are utilized and alterations to the purification, elution, and mass spectrometry-based analysis may also be made as the needs of the assay are altered as necessary.

Protein purification using the GST-GSH system relies on the high affinity of GST for immobilized GSH which allows selective protein purification (Hutchens, T. W., and Yip, T. T., J Inorg Biochem. 1; 42(2):105-18 (1990). Hutchens, T. W., and Yip T. T., J Chromatogr. 500:531-42 (1990)). The GSH is covalently coupled to Sepharose 4B via 10-carbon spacer arm. Sepharose is a crosslinked, beaded-form of agarose. GST can be appended to the amino or carboxyl terminal of a protein via recombinant DNA technology thus enabling affinity purification of the tagged protein based on GSH-GST interaction. Appropriate washing steps will reduce non-specific binding events to the GSH-sepharose matrix.

An affinity tagged recombinant immunophilin/FKBP or cyclophilin captured on the solid phase support will then be probed with non-denatured cell extracts either untreated or treated (either pre- or post lysis) with small molecule ligands that comprise the libraries for evaluation. Ligands may be evaluated as single agents or as groups of compounds. Cell lines for evaluation will preferentially be human but may also include any cell lines that express immunophilins. In some embodiments, cell lines may be both immortalized and represent the National Cancer Institute 60 panel screening set (NCI-60):

| Cell Line Name | Panel Name | Cell Line Name | Panel Name |
| --- | --- | --- | --- |
| CCRF-CEM | Leukemia | LOX IMVI | Melanoma |
| HL-60 (TB) | Leukemia | MALME-3M | Melanoma |
| K-562 | Leukemia | M14 | Melanoma |
| MOLT-4 | Leukemia | MDA-MB-435 | Melanoma |
| RPMI-8226 | Leukemia | SK-MEL-2 | Melanoma |
| SR | Leukemia | SK-MEL-28 | Melanoma |
| A549/ATCC | Non-Small Cell Lung | SK-MEL-5 | Melanoma |
| EKVX | Non-Small Cell Lung | UACC-257 | Melanoma |
| HOP-62 | Non-Small Cell Lung | UACC-62 | Melanoma |
| HOP-92 | Non-Small Cell Lung | IGR-OV1 | Ovarian |
| NCI-H226 | Non-Small Cell Lung | OVCAR-3 | Ovarian |
| NCI-H23 | Non-Small Cell Lung | OVCAR-4 | Ovarian |
| NCI-H322M | Non-Small Cell Lung | OVCAR-5 | Ovarian |
| NCI-H460 | Non-Small Cell Lung | OVCAR-8 | Ovarian |
| NCI-H522 | Non-Small Cell Lung | NCI/ADR-RES | Ovarian |
| COLO 205 | Colon | SK-OV-3 | Ovarian |
| HCC-2998 | Colon | 786-0 | Renal |
| HCT-116 | Colon | A498 | Renal |
| HCT-15 | Colon | ACHN | Renal |
| HT29 | Colon | CAKI-1 | Renal |
| KM12 | Colon | RXF 393 | Renal |
| SW-620 | Colon | SN12C | Renal |
| SF-268 | CNS | TK-10 | Renal |
| SF-295 | CNS | UO-31 | Renal |
| SF-539 | CNS | MCF7 | Breast |
| SNB-19 | CNS | MDA-MB-231/ATCC | Breast |
| SNB-75 | CNS | MDA-MB-468 | Breast |
| U251 | CNS | HS 578T | Breast |
| PC-3 | Prostate | MDA-N | Breast |
| DU-145 | Prostate | BT-549 | Breast |
|  |  | T-47D | Breast |

In some embodiments, immortalized cell lines are selected from the following:

| Cell Line Name | Panel Name | Cell Line Name | Panel Name |
|---|---|---|---|
| LXFL 529 | Non-Small Cell Lung | RPMI-7951 | Melanoma |
| DMS 114 | Small Cell Lung | M19-MEL | Melanoma |
| SHP-77 | Small Cell Lung | RXF-631 | Renal |
| DLD-1 | Colon | SN12K1 | Renal |
| KM20L2 | Colon | P388 | Leukemia |
| SNB-78 | CNS | P388/ADR | Leukemia |
| XF 498 | CNS | | |

Profiling could also involve additional immortalized cell lines of lymphoid, myeloid cardiac, neurona, pancreatic β muscle, fat cells and others cell types representative of different human organ and tissue types. Experiments may also use lysates from primary sources including cells of the immune system e.g. T, B, dendritic, nervous system e.g. cortical, hippocampal, and others. Appropriate washing steps will be used to reduce non-specific binding events followed by elution of the protein complexes from the affinity column using increasing concentrations of GSH, an affinity based-competitor of the GST epitope tag on the bait protein. The eluted material will then be evaluated via mass spectrometry.

Sample analysis requires tryptic digestion of the eluted material from the affinity column and subsequent analytical characterization using liquid chromatography-tandem mass spectrometry (LC-MS/MS) which is an analytical chemistry technique that combines the physical separation capabilities of liquid chromatography (or HPLC) with the mass analysis capabilities of mass spectrometry. LC-MS/MS has very high sensitivity and selectivity and it is used for determining masses of particles, for determining the elemental composition of a sample or molecule, and for elucidating the chemical constituents of molecules, including peptide sequences which can then be subsequently annotated into protein sequence via the use of database searches and highly refined algorithms such as Sequest, Mascot, OMSSA or others. The methods outlined above are meant to be representative but not exclusive technological solutions to affinity purification and protein identification. For recent reviews on the topic please see Liang, S. et al Current Proteomics 6:25-31 (2009).

Steps for carrying out a provided assay can be repeated with one or more Test Compounds, for example, with a library of Test Compounds. An assay with multiple Test Compounds can be carried out simultaneously or concurrently; or can be carried out simultaneously with some Test Compounds and then concurrently with others.

Test Compounds which increase the affinity of a binary complex for a target protein relative to the affinity of the Test Compound alone or a presenter protein alone can be selected for more advanced biological testing. Test Compounds selected for more advanced testing and Presentation Ligands are collectively referred to herein as "Ligand Compounds". Suitable selection criteria for more advanced testing include a two-fold, five-fold, ten-fold or twenty-fold increase in the affinity of a binary complex for a target protein relative to the affinity of a Test Compound alone or a presenter protein alone. For example, selected Test Compounds can be tested using in vitro assays to assess whether they increase or decrease the activity of a target protein and to assess the magnitude of the increase or decrease. Suitable in vitro assays will, of course, depend on a target protein and will likely require the presence of a presenter protein. In some embodiments, selected Test Compounds are tested in assays designed to assess efficacy against a disease condition or symptom(s) of a disease condition that is mediated by a target protein. For example, Test Compounds selected for their ability to modulate the activity of a target protein implicated in the development and maintenance of cancer can be assessed for their ability to inhibit the growth cancer cell lines. Suitable assays again will depend upon a target protein and are well known to the skilled artisan. Exemplary assays are provided in the following paragraphs.

Transcription Factors
Bcl-6
  Bcl-6 DNA binding and transcriptional activation
  The BCL6 proto-oncogene suppresses p53 expression in germinal-centre B cells. Phan, R T, Dalla-Favera R. (200.4). *Nature* 432(7017):635-9.
c-FOS
  c-FOS c-JUN interaction and luciferase reporter assay
  Kinetic studies of Fos-Jun.DNA complex formation: DNA binding prior to dimerization.
  Kohler J J, Schepartz A. *Biochemistry* 40(1):130-42 (2001).
  Cignal™ Reporter Assay Kit: A High Performance Tool for Assessing the Functions of Genes, Biologics and Small Molecule Compounds. Vikram Devgan, Abigail Harris, Qiong Jiang, and Scott Pattison. *SABiosciences Corporation* 6951 *Executive Way Frederick*, MD 21703 USA
c-JUN
  FOS/c-JUN interaction and luciferase reporter assay
  Kinetic studies of Fos-Jun.DNA complex formation: DNA binding prior to dimerization.
  Kohler J J, Schepartz A., *Biochemistry* 40(1):130-42 (2001).
  Cignal™ Reporter Assay Kit: A High Performance Tool for Assessing the Functions of Scott Pattison. *SABiosciences Corporation* 6951 *Executive Way Frederick*, MD 21703 USA
E2F1
  E2F1 DNA binding and transcriptional repression
  Transcriptional repression of the prosurvival endoplasmic reticulum chaperone
  GRP78/BIP by E2F1. Racek T, Buhlmann S, Rüst F, Knoll S, Alla V, Pützer BM. *J Biol Chem.* 283(49): 34305-14 (2008). Epub 2008 Oct. 7.
Hif-1a
  Hif-1a Reporter Assay
  TECHNICAL NOTE
  Cignal™ Reporter Assay Kit: A High Performance Tool for Assessing the Functions of Genes, Biologics and Small Molecule Compounds. Vikram Devgan, Abigail Harris, Qiong Jiang, and Scott Pattison. *SABiosciences Corporation* 6951 *Executive Way Frederick*, MD 21703 USA
  Chemiluminescent Hif-1a transcription factor assay (HRP-based)
  Identification of Small Molecule Inhibitors of Hypoxia-Inducible Factor 1
  Transcriptional Activation Pathway. Rapisarda, A., Uranchimeg, B., Scudiero, D. A., Selby, M., Sausville, E. A., Shoemaker, R. H., and Melillo, G. *Canc. Res.,* 62:4316-4324 (2002).

Hif-1a redistribution assay
  www.thermoscientific.jp/cellomics/redistribution/docs/hif-1alpha-u2os.pdf Flavonoids induce HIF-1alpha but impair its nuclear accumulation and activity. Triantafyllou A, Mylonis I, Simos G, Bonanou S, Tsakalof A. *Free Radic Biol Med.* 44(4):657-70 (2008). Epub 2007 Nov. 7.
Hif-1 ELISA
  www.activemotif.com/catalog/204/transam-hif-1.html
  Anti-angiogenic effects of SN38 (active metabolite of irinotecan): inhibition of hypoxia-inducible factor 1 alpha (HIF-1a/vascular endothelial growth factor (VEGF) expression of glioma and growth of endothelial cells.
  Hiroshi kamiyama, Shingo Takano, Koji Tsuboi and Akira Matsumura. Journal of Cancer Research and Clinical Oncology Volume 131, Number 4, 205-213 (2005)
Hif-2A
  Hif 2a and DNA binding
  Cooperative interaction of hypoxia-inducible factor-2alpha (1-HF-2alpha) and Ets-1 in the transcriptional activation of vascular endothelial growth factor receptor-2 (Flk-1). Elvert G, Kappel A, Heidenreich R, Englmeier U, Lanz S, Acker T, Rauter M, Plate K, Sieweke M. Breier G. *J Biol Chem.* 2003 Feb. 28; 278(9):7520-30 (2002). Epub 2002 Dec. 2.
MITF
  MITF DNA binding and transcriptional activation
  Microphthalmia-associated transcription factor is a critical transcriptional regulator of melanoma inhibitor of apoptosis in melanomas. Dynek J N, Chan S M, Liu J, Zha J, Fairbrother W J, Vucic D. *Cancer Res.;* 68(9): 3124-32 (2008).
  Construction of Protein Chip to Detect Binding of Mitf Protein (Microphthalmia Transcription Factor) and E-box DNA.
  Sang-Hee Yang, Jung-Sun Han, Seung-Hak Back, Eun-Young Kwak, Hae Jong Kim, Jeong-Hyun Shin, Bong-Hyun Chung and Eun-Ki Kim. *Applied Biochemistry and Biotechnology* Volume 151, Numbers 2-3, 273-282 (2008).
ChIP MITF
  STAT3 and MITE cooperatively induce cellular transformation through upregulation of c-fos expression. Akiko Joo, Hiroyuki Aburatani, Eiichi Morii, Hideo Iba and Akihiko Yoshimur *Oncogene* 23, 726-734 (2004).
Myc Family
  myc-responsive luciferase reporter
  TECHNICAL NOTE
  Cignal™ Reporter Assay Kit: A High Performance Tool for Assessing the Functions of Genes, Biologics and Small. Molecule Compounds. Vikram Devgan, Abigail Harris, Qiong Jiang, and Scott Pattison. *SABiosciences Corporation* 6951 *Executive Way Frederick,* MD 21703 USA
  FRET-based binding of tagged myc
  AlphaLISA Immunoassay Platform—the "No-Wash" High-Throughput Alternative to ELISA. Bielefeld-Sevigny, M. *Assay Drug Dev Technol* 7, 90-92 (2009).
  ELISA dsDNA for pulldown
  TEAL7 Inhibition of c-Myc Activity in Alternative Lengthening of Telomeres Regulates hTERT Expression. Kyle Lafferty-Whyte, Alan Bilsland, Stacey F Hoare, Sharon Burns, Nadia Zaffaroni, Claire J Cairney, and William Nicol Keith. *Neoplasia* 12(5): 405-414 (2010).

MLL-1
  MLL-1 and transcriptional regulatory activity
  Cooperativity in transcription factor binding to the coactivator CREB-binding protein (CBP). The mixed lineage leukemia protein (MLL) activation domain binds to an allosteric site on the KIX domain. Goto N K, Zor T, Martinez-Yamout M, Dyson H J, Wright P. E., *J Blot Chem.;* 277(45):43168-74 (2002). Epub 2002 Aug. 29.
  Domains with transcriptional regulatory activity within the ALLI and AF4 proteins involved in acute leukemia. R Prasad, T Yano, C Sorio, T Nakamura, R Rallapalli, Y Gu, D Leshkowitz, C M Croce, and E Canaani. *Proc Natl Acad Sci USA.* 92(26): 12160-12164 (1995).
Myb
  Protein-protein Interaction and transcriptional regulation
  Detection of proteins that bind to the leucine zipper motif of c-Myb, Favier I), Gonda T J. *Oncogene.* January; 9(1):305-11 (1994).
  Pim-1 kinase and p100 cooperate to enhance c-Myb activity. Leverson J D, Koskinen P J, Orrico F C, Rainio E M, Jalkanen K J, Dash A B, Eisenman R N, Ness S A. (1998). Mol *Cell.;* 2(4):417-25.
NF-κB
  DNA Binding and complex formation
  Competition between TRAF2 and TRAF6 regulates NF-kappaB activation in human B lymphocytes. Zhang W, Zhang X, Wu. X L, He L S, Zeng X F, Crammer A C, Lipsky P E, *Chin Med Sci J.* (1):1-12 (2010).
  Visualization of AP-1 NF-kappaB ternary complexes in living cells by using a BiFC-based FRET. Shyu Y J, Suarez C D, Hu C D. *Proc Natl Acad Sci US A.* 2008 Jan. 8; 105(1):151-6 (2008). Epub 2008 Jan. 2.
  TECHNICAL NOTE
  Cignal™ Reporter Assay Kit: A High Performance Tool for Assessing the Functions of and Scott Pattison. *SABiosciences Corporation* 6951 *Executive Way Frederick,* MD 21703 USA
Stat3
  DNA Binding and complex formation
  A novel small-molecule disrupts Stat3 SH2 domain-phosphotyrosine interactions and Stat3-dependent tumor processes. Zhang X, Yue P, Fletcher S. Zhao W, Gunning P T, Turkson J. *Biochem Pharmacol.;* 79(10): 1398-409 (2010). Epub 2010 Jan. 11.
  TECHNICAL NOTE
  Cignal™ Reporter Assay Kit: A High Performance Tool for Assessing the Functions of Genes, Biologics and Small Molecule Compounds. Vikram Devgan, Abigail Harris, Qiong Jiang, and Scott Pattison. *SABiosciences Corporation* 6951 *Executive Way* Frederick; MD 21703 USA
Stat5
  DNA Binding and complex formation
  Mammalian protein-protein interaction trap (MAPPIT) analysis of STAT5, CIS, and SOCS2 interactions with the growth hormone receptor. Uyttendaele I, Lemmens I, Verhee A, De Smet A S, Vandekerckhove J, Lavens D, Peelman. F, Tavernier *J. Mol Endocrinol.* (11):2821-31 (2007). Epub 2007 Jul. 31.
  TECHNICAL NOTE
  Cignal™ Reporter Assay Kit: A High Performance Tool for Assessing the Functions of Genes, Biologics and Small Molecule Compounds. Vikram Devgan, Abigail Harris, Qiong Jiang, and Scott Pattison. *SABiosciences Corporation* 6951 *Executive Way Frederick,* MD 21703 USA Wnt/Beta-Catenin
  Beta-Catenin Redistribution Assay—Nuclear Translocation of EGFP-Beta-Catenin
    Cadherin-bound beta-catenin feeds into the Wnt pathway upon adherens junctions dissociation: evidence for an intersection between beta-catenin pools. Kam Y, Quaranta V, *PLoS One;* 4(2):e4580 (2009). Epub 2009 Feb. 24,
Wnt/Beta-Catenin Signaling Via Fluorescent Reporter
  Fluorescence-based functional assay for Wnt/beta-cateninsignaling activity. Zhou. L, An N, Jiang W, Haydon R, Cheng H, Zhou Q, Breyer B, Feng T, He T C. *Biotechniques* 33(5):1126-8 (2002)
Nuclear Hormone Receptors
Androgen Receptor
  AR and Co-activators
    Cignal™ Reporter Assay Kit: A High Performance Tool for Assessing the Functions of Genes, Biologics and Small Molecule Compounds. Vikram Devgan, Abigail Harris, Qiong Jiang, and Scott Pattison. *SABiosciences Corporation* 6951 Executive Way Frederick; MD 21703 USA
    Functional screening of FxxLF-like peptide motifs identifies SMARCD1/BAF60a as an androgen receptor cofactor that modulates TMPRSS2 expression. van de Wijngaart D J, Dubbink H J, Molier M, de Vos C, Trapman J, Jenster G. *Mol Endocrinol.* (11):1776-86 (2009). Epub 2009 Sep. 17.
Estrogen Receptor
  ER and Co-Activators
    Cignal™ Reporter Assay Kit: A High Performance Tool for Assessing the Functions of nd Scott Pattison, *SABiosciences Corporation* 6951 Executive Way Frederick, MD 21703 USA
    A set of time-resolved fluorescence resonance energy transfer assays for the discovery of inhibitors of estrogen receptor-coactivator binding, Gunther J R, Du Y, Rhoden E, Lewis I, Revennaugh B, Moore T W, Kim S H, Dingledine R, Fu H, Katzenellenbogen J A. *J Biomol Screen.* (2):181-93 (2009), Epub 2009 Feb. 4.
Signal Transducers/Adaptors
Frizzled7
  Frizzled7 protein-protein interactions with PSD-95
  Direct interaction of Frizzled-1, -2, -4, and -7 with PDZ, domains of PSD-95. Hering H, & Sheng M, *FEBS Lett.;* 521(1-3):185-9 (2002).
Rab25
  Rab25 protein-protein interaction with growth factor receptors
  Emerging Role of RAB GTPases in Cancer and Human Disease. Kwai W, Cheng, John P. Lahad, Joseph W. Gray, and Gordon B. Mills. *Cancer Res.* 65; 2516 (2005).
  Development of new tools to comprehensively analyze mammalian Rabs in membrane traffic. Fukuda M. *Histol Histopathol.* (11):1473-80 (2010).
RAS and Raf
  Ras assay reagent—Raf1-RBD on agarose
  Minimal Ras-binding domain of RAF-1 can be used as an activation specific probe for Rasde Rooij, J and Bos, J. L. *Oncogene,* 14: 623-5 (1997)
  Ras GTPase Activation ELISA Kit—Raf1-RBD capture and anti-RAS+HRP Imatinib blocks migration and invasion of medulloblastoma cells by concurrently inhibiting activation of platelet-derived growth factor receptor and transactivation of epidermal growth factor receptor. Abouantoun T J, Macdonald T J. *Mol Cancer Ther.* Nov. 1, (2010).
  Raf1-RBD on beads
  Protein kinase C (PKC) βII induces cell invasion through a Ras/Mek-, PKC t/Rac 1-dependent signaling pathway, Zhang, J., Anastasiadis, P. Z., Liu, Y., Thompson, E. A. and Fields, A. P. *J. Biol. Chem.* 279, 22118-22123 (2004).
  Ras-Raf co-precipitation
  Critical Binding and Regulatory Interactions between Ras and Raf Occur through a Small, Stable N-Terminal Domainof Raf and Specific Ras Effector Residues. Chuang, E., Barnard, D., Hetfich, L. A., Zhang, X-F., Avruch, J., and Marshall, M. S. *Mol. Cell. Biol.*, Vol. 14, No. 8: 5318-5325 (1994).
Rho GDP Dissociation Inhibitor 2 (RhoGDI2)
  RhoGD12 and Rac-1 interaction
  RhoGDI2 as a therapeutic target in cancer Cho H J, Back K E, Yoo J. *Expert Opin Ther Targets.* 4(1):67-75 (2010).
PLD-1
  PLD-1 Protein-Protein interaction with PKCa
  Mechanisms of regulation of phospholipase D1 by protein kinase C alpha, Hu T, Exton J H. *J Biol Chem.* 278(4):2348-55 (2003).
PLD-2
  PLD-1 protein-protein interaction with PKCgamma-1
  The direct interaction of phospholipase C-gamma 1 with phospholipase D2 is important for epidermal growth factor signaling. Jang I H, Lee S, Park J B, Kim J H, Lee C S, Hur E M, Kim I S, Kim K T, Yagisawa H, Suh P G, Ryu S H. *J Biol Chem.* 278(20):18184-90 (2003). Epub 2003 Mar. 19.
Kinases
c-Src
  c-Src protein-protein interaction
  Focal Adhesion Kinase Overexpression Enhances Ras-dependent Integrin Signaling to ERK2/Mitogen-activated Protein Kinase through Interactions with and Activation of c-Src. David D. Schlaepfer and Tony Hunter, *J. Biol. Chem.* Vol. 272, 20: 13189-13195 (1997).
FAK
  AK protein-protein interaction
  Focal Adhesion Kinase Overexpression Enhances Ras-dependent Integrin Signaling to ERK2/Mitogen-activated Protein Kinase through Interactions with and Activation of c-Src. David D. Schlaepfer and Tony Hunter. *J. Biol. Chem.* Vol. 272, 20: 13189-13195 (1997).
P38
  Millipore—p38 MAP Kinase Assay
  Millipore's HCS231p38 MAP Kinase Assay provides a complete solution for identifying and quantifying the phosphorylation state of endogenous cellular p38
  www.millipore.com/catalogueitem/HCS231
  Many others commercially available
PKN3
  PKN3 catalytic activity.
  PKN3 is required for malignant prostate cell growth downstream of activated PI 3-kinase.
  Frauke Leenders,[1] Kristin Möpert,[1] Anett Schmieldeknecht,[1] Ansgar Santel,[1] Frank Czaudema,[1] Manuela Aleku,[1] Silke Penschuck,[1,*] Sibylle Dames,[1] Maria Stemberger,[1] Thomas Röhl,[1] Axel Wellmann, Wolfgang Arnold, Klaus Giese,[1] Jörg Kaufmann,[1] and Anke Klippel. *EMBO J.* 23(16):3303-3313 (2004). Published online 2004 Jul. 29

Pyk2-proline-rich tyrosine kinase-2

PyK2 and PDK1 protein-protein Interaction

Pyk2- and Src-dependent tyrosine phosphorylation of PDK1 regulates focal adhesions. Taniyama, Y., Weber, D. S., Roeic, P., Hilenski, L., Akers, M. L., Park, J., Hemmings, B. A., Alexander, R. W., Griendling, K. K. *Mol. Cell. Biol.* (22):8019-29 (2003).

RaLP

RalP protein-protein interaction

RaLP, a new member of the Src homology and collagen family, regulates cell migration and tumor growth of metastatic melanomas. Fagiani E, Giardina G, Luzi L, Cesaroni M, Quarto M, Capra M, Germano G, Bono M, Capillo M, Pelicci P, Lanfrancone L. *Cancer Res.;*67(7):3064-73 (2007).

ZAP-70

Zeta-chain-associated protein kinase 70

A Novel ZAP-70 Dependent FRET Based Biosensor Reveals Kinase Activity at both the Immunological Synapse and the Antisynapse Ran.driamampita C, Mouchacca P, Malissen B, Marguet D, Trautmann A, et al. *PLoS ONE* 3(1): e1521 (2008).

ZAP70 Kinase Enzyme System www.promega.com/Catalogue # V8311

Many others commercially available

Kinases General:

Ambit platform: www.ambitbio.com/Fluorescence lifetime after displacement of labeled staurosporine: jbx.sagepub.com/content/12/6/828.abstract FRET of tagged kinase (b/w labeled antibody and tracer)—Invitrogen LanthaScreen www.invitrogen.com/site/us/en/home/Products-and-Services/Applications/Drug-Di scovery IT arget-and-Lead-Identification-and-V alidation/KinaseBiology/Kinase-Activity-Assays/lanthascreentm-eu-kinase-binding-assay.html Tritium labeled pyridinyl imidazole: jbx.sagepub.com/content/4/3/129.abstract Cytokine, GF, TNF, Toll Receptors

IL-4R

Analysis of promoter regions regulating basal and interleukin-4-inducible expression of the human CB1 receptor gene in T lymphocytes, Börner C. Bedini A, Höllt V, Kraus J. *Mol Pharmacol.* 73(3):1013-9 (2008). Epub 2007 Dec. 21

IL-13R

Elevated IL-13Ralpha2 in intestinal epithelial cells from ulcerative colitis or colorectal cancer initiates MAPK pathway. Mandal D, Levine A D. *Inflamm Bowel Dis.,* 16(5):753-64 (2010).

IL-1R

MyD88, IRK1 and TRAF6 knockdown in human chondrocytes inhibits interleukin-1-induced matrix metalloproteinase-13 gene expression and promoter activity by impairing MAP kinase activation. R. Ahmad, J. Sylvester, and M. Zafarullah, "Cellular Signalling, vol. 19, no. 12, pp. 2549-2557 (2007).

IL-2R

Protein phosphatase 2A regulates interleukin-2 receptor complex formation and JAK3/STAT5 activation. Ross J A, Cheng Nagy Z S, Frost J A, Kirken R A. *J Biol Chem;* 285(6):3582-91 (2010). Epub 2009 Nov. 18.

IL-6R

The full-length leptin receptor has signaling capabilities of interleukin 6-type cytokine receptors. Baumann H, Morelia K K, White D W, Dembski M, Bailors P S, Kim H, Lai C F, Tartaglia L A. *Proc Natl Acad Sci USA.* 93(16):8374-8 (1996).

Cignal™ Reporter Assay Kit: A High Performance Tool for Assessing the Functions of d Scott Pattison. *SABiosciences Corporation* 69.51 Executive Way Frederick, MD 21703 USA

IGF-1R

A novel, potent, and selective insulin-like growth factor-I receptor kinase inhibitor blocks insulin-like growth factor-I receptor signaling in vitro and inhibits insulin-like growth, Gibson N W, Pachter J A. *Mol Cancer Ther.* 6 (8):2158-67 (2007). Epub 2007 Aug. 1.

TNF-R

NE-κB activation: TECHNICAL NOTE

Cignal™ Reporter Assay Kit: A High Performance Tool for Assessing the Functions of Genes, Biologics and Small Molecule Compounds. Vikram Devgan, Abigail Harris, Qiong Jiang, and Scott Pattison. *SABiosciences Corporation* 6951 Executive Way Frederick, MD 21703 USA

TLR4

LPS-TLR4 signaling to IRF-3/7 and NF-kappaB involves the toll adapters TRAM and TRIF. Fitzgerald K A, Rowe D C, Barnes B J, Caffrey D R, Visintin A, Latz E, Monks B, Pitha P M, Golenbock D T. *J Exp Med.;* 198(7):1043-55 (2003). Epub 2003 Sep. 29.

NE-κB activation: TECHNICAL NOTE

Cignal™ Reporter Assay Kit: A High Performance Tool for Assessing the Functions of Genes, Biologics and Small Molecule Compounds. Vikram Devgan, Abigail Harris, Qiong Jiang, and Scott Pattison. *SABiosciences Corporation* 6951 Executive Way Frederick, MD 21703 USA.

Miscellaneous

AAC-11

AAC-11 functional readout

The antiapoptotic protein AAC-11 interacts with and regulates Acinus-mediated DNA fragmentation. Rigou P, Piddubnyak V, Faye A, Rain J C, Michel L, Calvo F, Poyet J L. *EMBO J.* 28(11):1576-88 (2009). Epub 2009 Apr. 23.

CTLA4

CTLA4-targeting intracellular domain protein-protein interactions.

Targeting metastatic melanoma (2008) Poust J. Am J Health Syst Pharm. 2008 Dec. 15; 65(24 Suppl 9):S9-S15.

Inhibition of CTLA-4 function by the regulatory subunit of serine/threonine phosphatase 2A. Baroja M L, Vijayakrishnan L, Bettelli E, Darlington P J, Chau T A, Ling V, Collins M, Carreno B M, Madrenas J, Kuchroo V K., *J Immunol.;*168(10):5070-8 (2002).

EIF4E

EIF4E Activity and Protein-Protein Interaction

Regulation of eukaryotic initiation factor 4E (eIF4E) phosphorylation by mitogen-activated protein kinase occurs through modulation of Mnk1-eIF4G interaction. Shveygert M, Kaiser C, Bradrick S S, Grotneier M. *Mol Cell Biol.* (21):5160-7. Epub 2010 Sep. 7 (2010).

Ezh2-Histone Demethylase

Coordinated activities of wild-type plus mutant EZH2 drive tumor-associated hypertrimethylation of lysine 27 on histone H3 (H3K27) in human B-cell lymphomas. Sneeringer C J, Scott M P, Kuntz K W, Knutson S K, Pollock R M, Richon V M, Copeland R A. *Proc Natl Acad Sci.* (2010) Nov. 15. [Epub ahead of print]

IMPDH2
  Inhibition by mycopheolic acid
  Effect of mycophenolate acyl-glucuronide on human recombinant type 2 inosine monophosphate dehydrogenase. Gensburger O, Picard N, Marquet P. *Clin Chem.*;55(5):986-93 (2009). Epub 2009 Mar. 19.

Nav1.7
  Measure voltage-gated channel opening
  Characterization of voltage-gated sodium-channel blockers by electrical stimulation and fluorescence detection of membrane potential. Chien-Jung Huang, Alec Harootunian, Michael P Maher, Catherine Quan, Christopher D Raj, Ken McCormack, Randal Numann, Paul A Negulescu, & Jesús E González, *Nature Biotechnology* 24, 439-446 (2006).

NRLP3
  Manji G A, Wang L, Geddes B J, et al. "PYPAF1, a PYRIN-containing Apaf1-like protein that assembles with ASC and regulates activation of NF-kappa B.". *J Biol. Chem.* 277 (13): 11570-5 (2002)

PTP-1B
  Docking simulations and in vitro assay unveil potent inhibitory action of papaverine against protein tyrosine phosphatase 1B. Bustanji Y, Taha M O, Al-Macri I M, Mohammad M K. *Biol Pharm Bull.*;32(4):640-5 (2009).
  Synthesis, in vitro and computational studies of protein tyrosine phosphatase 1B inhibition of a small library of 2-arylsulfonylaminobenzothiazoles with antihyperglycemic activity. Navarrete-Vazquez G, Paoli P, León-Rivera I, Villalobos-Molina R, Medina-Franco J L, Ortiz-Andrade R, Estrada-Soto S, Camici G, Diaz-Coutiño D, Gallardo-Ortiz I, Martinez-Mayorga K, Moreno-Diaz H. *Bioorg Med Chem.* 17(9):3332-41 (2009). Epub 2009 Mar. 26.
  PTP1B Assay Kit, Colorimetric—EMD4Bio- sciences|EMD Chemicals USA A colorimetric assay kit to measure PTP1B activity.

In many instances, drug candidates are developed having good efficacy against a desired target protein, only to fail during their drug development when it is discovered that they also have an undesired activity against a second target protein, leading to unacceptable side effects. For ease of reference, these drug candidates are referred to as "modulator compounds". In some embodiments, the present invention provides methods of developing a drug candidate with modified selectivity towards a first target protein relative to a second target protein from a modulator compound that modulates the activity of both the first and second target proteins. The methods disclosed herein provide, among other things, methods for modifying the structure of modulator compounds to develop new drug candidates having increased selectivity for a desired target and decreased activity towards a undesired target. In some embodiments, a method utilizes a Ligand Compound complexed with a presenter protein to a form binary compound with enhanced binding affinity towards a desired target protein relative to an undesired target protein.

As discussed above, a Ligand Compound comprises a Presenter Interacting Moiety (a Conserved Region) and a Target Interacting Moiety (Variable Region). A Presenter Interacting Moiety binds to a presenter protein to form a binary complex; and a Target Interacting Moiety enhances the affinity of the resulting binary complex for a desired target protein relative to the affinity of a presenter protein for a desired target protein in the absence of the binary complex. In some embodiments, a Target Interacting Moiety is selected so that it does not substantially bind to an undesired target protein, e.g., binds to an undesired target protein with a $K_d$ greater than 1 μM, preferably with a $K_d$ greater than 10 μM in some embodiments, a Modulator Compound is covalently associated (bonded) to a Target interacting Moiety of a Ligand Compound to form a modified Ligand Compound. "Covalently associating" a Modulator Compound to a Target Interacting Moiety of a Ligand. Compound means that there is a covalent bond between a Target Interacting Moiety and a Modulator Compound. In some embodiments, a Modulator Compound is connected to a Target Interacting Moiety by a linker group. In some embodiments, a Modulator Compound is incorporated within a Target Interacting Moiety as part of the macrocylic ring itself. In some embodiments, a Modulator Compound is covalently bonded to two distinct ring atoms in a Target Interacting Moiety and is the only group which intervenes between these two ring atoms.

In some embodiments, after formation of a modified Ligand Compound, a presenter protein and a modified Ligand Compound are combined under conditions suitable for formation of a binary complex, referred to herein as a "modified binary complex". Because a Modulator Compound is bonded to a Target Interacting Moiety, a Presenter Interacting Moiety remains free to bind with a presenter protein. As such, conditions described above for forming a binary complex with a Test Compound are suitable for use in forming a modified binary complex with a modified Ligand Compound. Because a binary complex of a Ligand Compound and a presenter protein shows selectivity towards a first target protein relative to a second target protein, associating the Modulator Compound with a binary complex will similarly impart a Modulator Compound with selectivity towards a desired first target. In certain embodiments, interacting sites form contacts between the target protein and the modulator compound, and the target protein and the Target Interacting Moiety. In certain embodiments, interacting sites form contacts between the target protein and the modulator compound, the target protein and the Target Interacting Moiety, and the target protein and the presenter protein.

The activity of a first target protein is then measured in the presence of a modified binary complex and in the presence of a modulator compound (alone, e.g., in the absence of a modified binary complex); and the activity of a second protein is then measured in the presence of a modified binary complex and in the presence of a modulator compound (alone, e.g., in the absence of a modified binary complex). Methods for measuring the activity of a second target protein are as described above for assays utilizing a Test Compound. The activity of first and second target proteins in the presence of a modified binary complex and the activity of first and second target proteins in the presence of a modulator compound (alone, e.g., without the modified binary complex) are compared to assess whether a modified ligand compound has altered selectivity towards a first target protein relative to a second target protein compared with a modulator compound. Modified binary complexes that show increased selectivity for a desired target protein can then be selected and tested in more advanced biological assays, as described above for Test Compounds.

The steps of the method can be repeated with additional modified binary complexes or by preparing additional modified Ligand Compounds and testing them according to the steps just described. The activity of a modified binary complex and its selectivity for a desired target protein relative to an undesired target protein can be influenced by how a Modulator Compound is associated with a Ligand Compound, e.g., where a Modulator Compound is attached, whether it is directly bonded to the Target Interacting Moiety of the Ligand Compound, incorporated into a Target Interacting Moiety of a Ligand Compound, or whether it is connected to a Target interacting Moiety of a Ligand Compound through a linker group and the positioning of the attachment. Where a linker is present, the length, size and nature of the linker can also influence activity and selectivity. As such, it is desirable to repeat the assay with multiple modified binary complexes, e.g., wherein the point of association, the means of association and, where present, the length, size and nature of the linker are varied. Alternatively, or in addition to, the structure of a modulator compound and/or a Target Interacting Moiety of a Ligand Compound can be varied. Where a plurality of modified binary complexes are tested, e.g., as in a library, compounds can be tested simultaneously, concurrently or some simultaneously and others concurrently.

The relevant teachings of the publications discussed herein are incorporated herein by reference.

The invention is illustrated by the following examples, which are not intended to be limiting in any way.

EXEMPLIFICATION

Sequence validated cDNAs encoding the collection of either human immunophilins/FKBPS (FKBP12, FKBP12.6, FKBP13, FKBP19, FKBP22, FKBP23, FKBP25, FKBP36, FKBP38, FKBP51, FKBP52, FKBP60 and FKBP65) or cyclophilins (Cyp-A, PPIL1, PPIL3, USA-Cyp, Cyp-F, Cyp-B, Cyp-C, Cyp29, Cyp33, Cyp40, SDCCAG10, Cyp57, Cyp60, HAL539, Cyp88, NK-Cyp and RanBP) can be acquired from commercial sources (Origen, Inc.). Standard molecular biology techniques can be utilized to clone the cDNA into an appropriate vector for expression in bacteria. One such vector is pEX-N-GST (Origen) that will result in an open reading frame (ORF) with an amino terminal GST affinity tag. GST-tags are often used for affinity purification of recombinant proteins expressed in *Escherichia coli* and other prokaryotic expression systems. The cloning vector pEX-N-GST also contains an isopropyl-β-D-thio-galactoside (IPTG) regulated promoter to induce expression of the cloned ORF. If desired, an ORF containing a carboxy terminal GST affinity tag can be generated using an alternatively designed vector. Additional cloning vectors could also be chosen that will append the amino or carboxy terminus of the ORF with an alternative affinity tag e.g. poly-histidine, Flag, DDK, and others. The vector containing the affinity tagged ORF (FKBP or cyclophilin) can be transformed into an appropriate expression strain such as *E. coli* BL21/DE3 using standard methods, Bacterial growth and where appropriate IPTG-induction is perfumed. Bacterial cells are harvested via centrifugation and the resulting cell pellet lysed either by physical means or by means of detergents and enzymes such as lysozyme followed by centrifugation to generate a cleared cell lysate. The GST-tagged proteins can be purified from the cleared bacterial extract by chromatography over a glutathione (GSH)-agarose column (GE HealthCare) or via use of GSH magnetic resins (Pierce) or other GSH affinity capture methods. Each method will utilize kit recommended buffers and conditions. However, each method consists of a general set of steps that enable binding of the GST tagged protein to the GSH solid support followed by appropriate washing steps to remove unwanted non-specific binding proteins. These steps provide a prepared affinity captured GST-tagged protein to be used for subsequent experimentation. Moreover, captured GST-tagged fusion protein can be eluted with PBS containing 30 mM GSH to allow the purified tagged immunophilins and cyclophilins to be evaluated for both natural ligand binding (rapamycin, FK506 or cyclosporin) and peptidyl-prolyl isomerase activity as described in Liu, J., Albers, M. W., Chen, C.-M., Schreiber, S. L., & Walsh, C. T. *Proc. Natl. Acad. Sci.* USA 87, 2304-2308 (1990); Liu, J., Farmer, J. D., Jr., Lane, W. S., Friedman, J., Weissman, I., & Schreiber, S. L. Calcineurin is a common target of Cyclophilin-cyclosporin A and FKBP-FK506 complexes. *Cell* 66, 807-815 (1991).

Mammalian cell extracts can be generated using standard commercially available kits such as CytoBuster Protein Extraction Reagent (Novagen Inc). Briefly, lysates prepared from adherent cells required removal of culture medium, two washes with phosphate buffered saline followed by addition of the recommended amount of a non-denaturing mammalian cell lysis reagent plus an appropriate protease inhibitor cocktail (see product insert for lysis conditions); generally 5 min at 4° C. Cell debris are collected by centrifugation for 5 min at 16,000×g (4° C.). Supernatant is recovered for subsequent experimental analysis. Generating cell lysates from non-adherent cells requires a slow speed centrifugation step (2,000×g) for 5 min to collect cells and subsequent method application as described above.

The mammalian cell extracts (0.4-4.0 mg protein/ml) can be pre-cleared by a 1 hr pre-incubation with GSH-sepahose using a 1:100 ration of extract to sepharose resin) at 4° C. followed by a centrifugation step. This step will remove the endogenous glutathione binding proteins including GST. The cleared extracts can then be mixed with the immobilized tagged proteins and gently mixed for 1 hr in the absence or presence of 10 μM of the individual Test Compounds. The GSH solid support can be washed via methods specific for each manufacturers product but generally entail intermittent centrifugation and washing steps with a buffer such as PBS containing a mild detergent such as 0.02% Nonidet P-40 or 0.2% Triton X-100. The washed GSH bound protein complexes can then be eluted via the use of 30-50 mM glutathione and prepared for mass spectrometry analysis.

Tandem mass spectrometer can "sequence" a peptide ion by first measuring the mass of the peptide and then selectively isolating and gently fragmenting that peptide at peptide bonds followed by mass measurement of the fragment ions. The resulting tandem mass spectrum contains the sequence information for a single peptide. For mass spectrometry analysis, the eluted protein complexes can be dialyzed to remove excess GSH. Proteins can then be TCA precipitated, trypsinized, and subsequently purified using Empore C18 extraction media (3M), and analyzed via. LC-MS/MS; for example via use of a LTQ linear ion trap mass spectrometer (ThermoFinnigan) using an 18 cm×125 μm (ID) C18 column and a 50 minute 8%-26% acetonitrile gradient. Spectra can then searched using highly refined algorithms such as Sequest, Mascot, OMSSA or others against a target-decoy human tryptic peptide database to search and enable protein identification. Methods for each approach are as described in Bauer, A and Kuster, B., Affinity purification-mass spectrometry: Powerful tools for the characterization of protein complexes *Eur. J. Blochem.* 270, 570-578 (2003); Chang I. F., Mass spectrometry-based proteornic analysis of the epitope-tag affinity purified protein complexes in eukaryotes Current Proteomics 6, 6158-6166 (2006); Sowa, M. E., Bennett, E J., Gygi, S. P., and Harper J. W, Defining the Human Deubiquitinating Enzyme Interaction Landscape *Cell;* 138(2): 389-403(2009).

If Test Compound dependent target proteins are identified, further studies are performed to determine whether there is measurable difference in affinity for the Test Compound and the identified target in the absence versus the presence of the presenter protein. Standard methods for this approach include calculation of the dissociation constant ($K_d$), The $K_d$ is a specific type of equilibrium constant that measures the propensity of a larger object to separate (dissociate) reversibly into smaller components, as when a complex falls apart into its component molecules.

There are multiple established technical methods to calculate $K_d$ (reviewed in Stockwell, B. R. *Nature;* 432 (7019): 846-54 (2004)) and have applicability to generate data to address questions as highlighted above. Specific techniques such as Surface Plasmon Resonance (SPR) and fluorescence Polarization (FP) may represent preferred but not exclusive methodologies for calculating $K_d$. SPR measures the change in refractivity of a metal surface when a compound binds to a protein that is immobilized on that metal surface (Homola, J., *Annal. Bioanal. Chem.;* 377: 528-539 (2003)) while FP measures the change in tumbling rate for a compound when it is bound to a protein using toss-of-polarization of incident light (Burke, T. J., et. al, *Comb. Chem. High Throughput Screen;* 6: 183-194 (2003)). Each of these technologies has proven amenable to calculating the $K_d$ of protein-drug-protein complexes (Banaszynski, L. A., et. al. *J. Am. Chem. Soc.;* 127: 4715-4721 (2005).

Experiments are also performed to define whether formation of the presenter protein-test compound interaction with the captured target results in modulation of the normal activity of the target. These methods will be target specific and non-exhaustive examples have been provided in a proceeding section of this document.

What is claimed is:

1. A method of modulating the activity of K-Ras, said method comprising contacting a compound and a presenter protein under suitable conditions to produce a complex, wherein the complex binds to K-Ras and the compound has the formula:

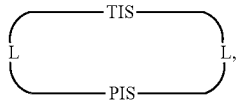

wherein:

the compound comprises between 18 and 30 ring atoms, wherein each of the ring atoms is selected from the group consisting of oxygen, nitrogen, carbon, sulfur, and phosphorus;

each L is independently a bond or a bivalent substituted or unsubstituted portion of the compound;

the TIS is a Target Interacting Site that contacts one or more corresponding interacting sites on K-Ras; and the PIS is a Presenter Interacting Site that contacts one or more corresponding interacting sites on the presenter protein, and wherein the PIS comprises the formula selected from the formulas consisting of (A), (B) and (C):

(i)

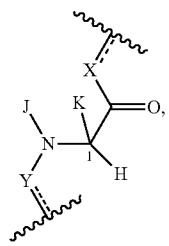

(A)

wherein:

J is hydrogen or (C1-C2) alkyl;

K is (C1-C4)-straight or branched alkyl, benzyl or cyclohexylmethyl; or wherein J and K may be taken together to form a 5-7 membered heterocyclic ring which may contain an O, S, SO or $SO_2$ substituent therein;

the stereochemistry at carbon position 1 is R or S;

X is selected from —NH—, —N(alkyl)-, —O—, —C(O)—, —CHOH—, —CH=, or —$CH_2$—;

Y is selected from —C(O)NH—, —C(O)N(alkyl)-, —C(O)O—, —C(O)C(O)—, —C(O)CHOH—, —C(O)CH=, —C(O)$CH_2$—, and —S(O)$_2$; and ===== represents a single or a double bond; and the points of attachment to the rest of the compound are through a terminus of each L; and (ii)

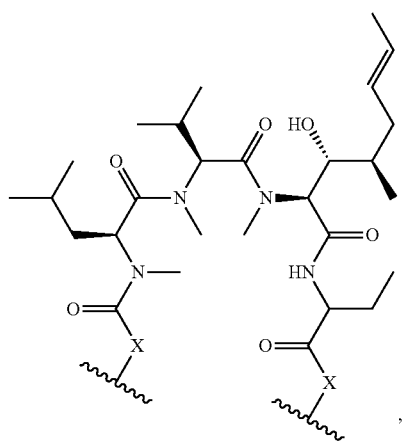

(B)

wherein:

each X is independently selected from —NH—, —N(alkyl)-, —O—, —C(O)—, —CHOH—, or —$CH_2$—; and the points of attachment to the rest of the compound is by a covalent bond to a terminus of each L; and (iii)

(C)

[Chemical structure showing a compound with formula (C) containing a piperidazine ring with X-C(=O) group, NH linkage, amide bonds, R¹ substituent, and a hydroxyphenyl group with (R²)ₘ substituents]

wherein:
- X is selected from —NH—, —N(alkyl)-, —O—, —C(O)—, —CHOH—, or —CH$_2$—,
- R$^1$ is selected from (C1-C6)-alkyl, (C1-C6)-alkenyl, (C1-C6)-alkynyl, aryl, (C3-C7)-carbocyclyl, —(C1-C4 alkylene)-aryl, and —(C1-C4 alkylene)-(C3-C7) carbocyclyl;
- each R$^2$ is independently selected from halo, —C≡N, C1-C4 alkyl, =O, C$_3$-C$_7$ cycloalkyl, C$_1$-C$_4$ alkyl, —OH, —O—(C$_1$-C$_4$ alkyl), —SH, —S—(C$_1$-C$_4$ alkyl), —(C$_1$-C$_4$ alkyl)-N(R$^b$)(R$^b$), —N(R$^b$)(R$^b$), —O—(C$_1$-C$_4$ alkyl)-N(R$^b$)(R$^b$), —(C$_1$-C$_4$ alkyl)-O—(C$_1$-C$_4$ alkyl)-N(R$^b$)(R$^b$), —C(O)—N(R$^b$)(R$^b$), —(C$_1$-C$_4$ alkyl)-C(O)—N(R$^b$)(R$^b$), —O-(heteroaryl), —O-(heterocycle), —O-phenyl, -heteroaryl, -heterocycle, and -phenyl, wherein:
  each R$^b$ is independently selected from hydrogen, and —C$_1$-C$_4$ alkyl; or two R$^b$ are taken together with the nitrogen atom to which they are bound to form a 4- to 8-membered saturated heterocycle optionally comprising one additional heteroatom selected from N, S, S(=O), S(=O)$_2$, and 0,
  any alkyl substituent is optionally further substituted with one or more of —OH, —O—(C$_1$-C$_4$ alkyl), halo, —NH$_2$, —NH(C$_1$-C$_4$ alkyl), or —N(C$_1$-C$_4$ alkyl)$_2$; and
  any carbon atom on a phenyl, cycloalkyl, heteroaryl or heterocycle substituent is optionally further substituted with one or more of —(C$_1$-C$_4$ alkyl), —(C$_1$-C$_4$ fluoroalkyl), —OH, —O—(C$_1$-C$_4$ alkyl), —O—(C$_1$-C$_4$ fluoroalkyl), halo, —NH$_2$, —NH(C$_1$-C$_4$ alkyl), or —N(C$_1$-C$_4$ alkyl)$_2$;
- m is 0, 1, 2 or 3; and
- the points of attachment to the rest of the compound is by a covalent bond to a terminus of each L;
- wherein each L is independently selected from a bond and a linear chain of up to 10 atoms, independently selected from carbon, nitrogen, oxygen, sulfur or phosphorous atoms, wherein each atom in the chain is optionally substituted with one or more substituents independently selected from alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and wherein any two atoms in the chain may be taken together with the substituents bound thereto to form a ring, wherein the ring may be further substituted and/or fused to one or more optionally substituted carbocyclic, heterocyclic, aryl or heteroaryl rings; and
- wherein when the PIS has formula (A) the presenter protein is a member of the FKBP family, and when the PIS has formula (B) or (C), the presenter protein is a member of the cyclophilin family.

2. The method of claim 1, wherein the presenter protein is a member of the FKBP family.

3. The method of claim 2, wherein the PIS has the structure of formula (A).

4. The method of claim 1, wherein the presenter protein is a member of the cyclophilin family.

5. The method of claim 4, wherein the PIS has the structure of formula (B) or (C).

6. The method of claim 1, wherein the complex binds K-Ras with at least a two-fold increase in affinity relative to the affinity of the compound for K-Ras in the absence of the presenter protein.

\* \* \* \* \*